US010982267B2

(12) United States Patent
Li et al.

(10) Patent No.: US 10,982,267 B2
(45) Date of Patent: Apr. 20, 2021

(54) LUMINOPHORE-LABELED MOLECULES COUPLED WITH PARTICLES FOR MICROARRAY-BASED ASSAYS

(71) Applicants: CAPITALBIO TECHNOLOGY CORPORATION, Beijing (CN); TSINGHUA UNIVERSITY, Beijing (CN)

(72) Inventors: Yang Li, Beijing (CN); Guanbin Zhang, Beijing (CN); Di Jiang, Beijing (CN); Guangxin Xiang, Beijing (CN); Wanli Xing, Beijing (CN); Jing Cheng, Beijing (CN)

(73) Assignees: CAPITALBIO TECHNOLOGY CORPORATION, Beijing (CN); TSINGHUA UNIVERSITY, Beiting (CN)

( * ) Notice: Subject to any disclaimer, the term of this patent is extended or adjusted under 35 U.S.C. 154(b) by 91 days.

(21) Appl. No.: 16/197,318

(22) Filed: Nov. 20, 2018

(65) Prior Publication Data
US 2019/0185922 A1 Jun. 20, 2019

Related U.S. Application Data

(62) Division of application No. 15/100,970, filed as application No. PCT/CN2014/001085 on Dec. 2, 2014, now Pat. No. 10,167,499.

(30) Foreign Application Priority Data

Dec. 5, 2013 (CN) .......................... 201310651906.5

(51) Int. Cl.
*C12Q 1/6837* (2018.01)
*G01N 33/58* (2006.01)
*C12Q 1/6883* (2018.01)
*C12Q 1/6825* (2018.01)
*C12Q 1/6827* (2018.01)
*C12Q 1/6886* (2018.01)

(52) U.S. Cl.
CPC ......... *C12Q 1/6837* (2013.01); *C12Q 1/6825* (2013.01); *C12Q 1/6827* (2013.01); *C12Q 1/6883* (2013.01); *C12Q 1/6886* (2013.01); *G01N 33/58* (2013.01); *C12Q 2600/156* (2013.01); *C12Q 2600/158* (2013.01); *C12Q 2600/16* (2013.01)

(58) Field of Classification Search
CPC .............................. C12Q 1/6837; G01N 33/58
See application file for complete search history.

(56) References Cited

U.S. PATENT DOCUMENTS 6,803,196 B1 10/2004 Lyon et al.
2007/0048762 A1 3/2007 Hashmi et al.

FOREIGN PATENT DOCUMENTS

| CN | 1553186 A | 12/2004 |
|---|---|---|
| CN | 1566366 A | 1/2005 |
| CN | 1580283 A | 2/2005 |
| CN | 1643379 A | 7/2005 |
| CN | 1548549 A | 11/2005 |
| CN | 1699595 A | 11/2005 |
| CN | 101445834 A | 6/2009 |
| CN | 101586150 A | 11/2009 |
| CN | 101680893 A | 3/2010 |
| CN | 102220434 A | 10/2011 |
| CN | 102373265 A | 3/2012 |
| CN | 102453761 A | 5/2012 |
| CN | 102534031 A | 7/2012 |
| CN | 103760355 A | 4/2014 |
| EP | 1 288 664 A1 | 3/2003 |
| EP | 1 589 105 A1 | 10/2005 |
| JP | 2003159057 A | 6/2003 |
| WO | 00/33062 A1 | 6/2000 |
| WO | 00/47322 A2 | 8/2000 |
| WO | 00/54882 A1 | 9/2000 |
| WO | 00/58516 A2 | 10/2000 |
| WO | 01/27327 A2 | 4/2001 |
| WO | 01/27329 A2 | 4/2001 |
| WO | 02/28523 A2 | 4/2002 |

(Continued)

OTHER PUBLICATIONS

Son et al, Quantitative DNA hybridization in solution using magnetic/luminescent core-shell nanoparticles, 2007, Analytical Biochemistry, 370, 186-194. (Year: 2007).*
CN, 1st Search Report for CN patent application 2013106519065, dated Jan. 15, 2015, 2 pages.
CN, 1st Office Action for CN patent application 2013106519065, dated Feb. 6, 2015, 5 pages with additional 8 pages of an English language equivalent or summary.
CN, Notice of Grant for CN patent application 2013106519065, dated Jul. 31, 2015, 1 page and additional 2 pages of an English language equivalent or summary.
EP, Response to 1st Office Action for EP application 14 867 063.1, dated Jun. 26, 2018, 12 pages.

(Continued)

Primary Examiner — Narayan K Bhat
(74) Attorney, Agent, or Firm — Rimon, P.C.

(57) ABSTRACT

A method for labeling target molecules coupled to particles for the detection of the target molecules using a microarray chip, comprises: providing a functionalized microparticle, wherein the microparticle is coated with one or more functional group; providing a modification group on each of the target molecules to be detected to form modified target molecules; contacting the functionalized microparticle with the modified target molecules; coupling a luminophore to the complex between the functionalized microparticle and the modified target molecules, thereby directly or indirectly labeling each modified target molecules with the luminophore. By directly or indirectly labeling the target molecules with the luminophore, the method reduces the cost of fluorescence detection, and avoids PCR inhibition derived from traditional fluorescence labeling molecules.

2 Claims, 6 Drawing Sheets

Specification includes a Sequence Listing.

(56) References Cited

FOREIGN PATENT DOCUMENTS

| WO | 02/068684 A2 | 9/2002 |
|---|---|---|
| WO | 2004/106357 A1 | 12/2004 |
| WO | 2007038578 A1 | 4/2007 |
| WO | 2007/092538 A2 | 8/2007 |
| WO | 2012/016357 A1 | 2/2012 |
| WO | 2012/055069 A1 | 5/2012 |
| WO | 2015/081612 A1 | 6/2015 |

OTHER PUBLICATIONS

EP, 2nd Office Action for EP application 14 867 063.1, dated Oct. 8, 2018, 5 pages.
EP, Supplemental Search Report for EP application 14 867 063.1, dated Mar. 23, 2017, 7 pages.
U.S. Notification of References Citied by examiner for U.S. Appl. No. 15/100,970, dated Aug. 11, 2017-Nov. 12, 2018, 4 pages.
Choi et al. (Kim), "Application of allele-specific primer extension-based microarray for simultaneous multi-gene mutation screening in patients with non-syndromic hearing loss," International Journal of Molecular Medicine 25: 315-320, 2010 XP055358171, GR ISSN: 1107-3756, DOI: 10.3892/ijmm_00000347.
Xiong et al, "A Melting Curve Analysis-Based PCR Assay for One-Step Genotyping of beta Thalassemia Mutations," The Journal of Molecular Diagnostics, 2011, 13, p. 427-435.
Zhang et al. "Validation of a mobile phone-assisted microarray decoding platform for signal-enhanced mutation detection11," Biosensors and Bioelectronics, Elsevier BV, NL, vol. 26, No. 12, May 23, 2011, p. 4708-4714 XP028242164, ISSN: 0956-5663, DOI: 10.1016/J.BIOS.2011.05.031 [retrieved on May 27, 2011].
Ashkin et al., "Internal cell manipulation using infrared laser traps," Proc. Natl. Acad. Sci. USA, Oct. 1989, vol. 86, pp. 7914-7918.
Fan et al., "Highly parallel genomic assays," Nature Reviews Genetics, Aug. 2006, vol. 7, pp. 632-644.
Gao et al., "Comparison of Different Methods for Preparing Single Stranded DNA for Oligonucleotide Microarray," Analytical Letters, 2003, vol. 33, No. 13, pp. 2849-2863.
Gerry et al., "Universal DNA Microarray Method for Multiplex Detection of Low Abundance Point Mutations,"J. Mol. Biol., 1999, vol. 292, pp. 251-262.
Gonzalez et al., "Somatic Microindels: Analysis in Mouse Soma and Comparison With the Human Germline," Human Mutation, 2007, vol. 28, No. 1, pp. 69-80.
Heller, "DNA Microarray Technology: Devices, Systems, and Applications," Annu. Rev. Biomed. Eng., 2002, vol. 4, pp. 129-153.
Hoheisel, "Microarray technology: beyond transcript profiling and genotype analysis," Nature Reviews Genetics, Mar. 2006, vol. 7, pp. 200-210.
Kanehisa, "Use of statistical criteria for screening potential homologies in nucleic acid sequences," Nucleic Acids Research, 1984, vol. 12, No. 1, pp. 203-213.
Kurt et al., "Multiplexed Genotyping of Methicillin-Resistant *Staphylococcus aureus* Isolates by Use of Padlock Probes and Tag Microarrays," Journal of Clinical Microbiology, Mar. 2009, vol. 47, No. 3, pp. 577-585.
Leach et al., "Theoretical Investigations of Novel Nucleic Acid Bases," J. Am. Chem. Soc., 1992, vol. 114, No. 10, pp. 3675-3683.
Li et al., "Construction of a Multiplex Allele-Specific PCR-Based Universal Array (ASPUA) and Its Application to Hearing Loss Screening," Human Mutation, 2008, vol. 29, No. 2, pp. 306-314.
Lim et al., "Photocleavage Based Affinity Purification and Printing of Cell-free Expressed Proteins: Application to Proteome Microarrays," Anal Biochem., Dec. 2008, vol. 383, No. 1, pp. 103-115.
Liu et al., "An integrated and sensitive detection platform for biosensing application based on Fe@Au magnetic nanoparticles as bead array carries," Biosensors and Bioelectronics, 2010, vol. 26, pp. 1442-1448.

Mantsch et al., "Structural and Enzymatic Properties of Adenine 1-Oxide Nucleotides," Biochemistry, 1975, vol. 14, No. 26, pp. 5593-5601.
Marshall et al., "DNA chips: An array of possibilities," Nature Biotechnology, Jan. 1998, vol. 16, pp. 27-31.
Matson et al., "Biopolymer Synthesis on Polypropylene Supports: Oligonucleotide Arrays," Analytical Biochemistry, 1995, vol. 224, pp. 110-116.
Matteucci et al., "Synthesis of Deoxyoligonudeotides on a Polymer Support," J. Am. Chem. Soc., 1981, vol. 103, No. 11, pp. 3185-3191.
Milligan et al., "Current Concepts in Antisense Drug Design," Journal of Medicinal Chemistry, Jul. 1993, vol. 36, No. 14, pp. 1923-1937.
Mulvaney et al., "Direct detection of genomic DNA with fluidic force discrimination assays," Analytical Biochemistry, 2009, vol. 392, pp. 139-144.
Riccelli et al., "Hybridization of single-stranded DNA targets to immobilized complementary DNA probes: comparison of hairpin versus linear capture probes," Nucleic Acids Research, 2001, vol. 29, No. 4, pp. 996-1004.
Schena et al., "Parallel human genome analysis: Microarray-based expression monitoring of 1000 genes," Proc. Natl. Acad. Sci. USA, Oct. 1996, vol. 93, pp. 10614-10619.
Shaw et al., "Modified deoxyoligonucleotides stable to exonuclease degradation in serum," Nucleic Acids Research, 1991, vol. 19, No. 4, pp. 747-750.
Xu et al., "Protein and Chemical Microarrays—Powerful Tools for Proteomics," Journal of Biomedicine and Biotechnology, 2003, vol. 5, pp. 257-266.
Zhu et al., "Multiplex Asymmetric PCR-Based Oligonucleotide Microarray for Detection of Drug Resistance Genes Containing Single Mutations in Enterobacteriaceae," Antimicrobial Agents and Chemotherapy, Oct. 2007, vol. 51, No. 10, pp. 3707-3713.
Zhang et al., "Validation of a mobile phone-assisted microarray decoding platform for signal-enhanced mutation detection," Aug. 2011, vol. 26, pp. 4708-4714.
State Intellectual Property Office of the People's Republic of China, International Search Report for Int'l Appl'n No. PCT/CN2010/001711, dated Aug. 11, 2011, 5 pages.
The International Bureau of WIPO, International Preliminary Report on Patentability for Int'l Appl'n No. PCT/CN2010/001711, dated Apr. 30, 2013, 6 pages.
State Intellectual Property Office of the People's Republic of China, International Search Report for Int'l Appl'n No. PCT/CN2014/001085, dated Mar. 10, 2015, 5 pages.
State Intellectual Property Office of the People's Republic of China, Written Opinion for Int'l Appl'n No. PCT/CN2014/001085, dated Mar. 10, 2015, 5 pages.
The International Bureau of WIPO, International Preliminary Report on Patentability for Int'l Appl'n No. PCT/CN2014/001085, dated Jun. 7, 2016, 6 pages.
European Patent Office, Response to the Communication Pursuant to Rules 70(2) and 70a(2) EPC for Application No. EP 14867063.1, dated Nov. 6, 2017, 13 pages.
European Patent Office, Supplementary European Search Report for Application No. EP 14867063, dated Mar. 23, 2017, 2 pages.
European Patent Office, Communication Pursuant to Article 94(3) EPC for Application No. EP 14867063.1, dated Feb. 20, 2018, 7 pages.
Summons to attend oral proceedings pursuant to Rule 115(1) EPC for European patent application EP14/867,063.1, dated Oct. 9, 2019, 6 pages.
Response to the summons to attend oral proceedings pursuant to Rule 115(1) EPC for European patent application EP14/867,063.1, dated Jan. 9, 2020, 8 pages.
Claims (1st auxiliary request—markup version) for European patent application EP14/867,063.1, dated Jan. 9, 2020, 2 pages.
Claims (1st auxiliary request—clear version)for European patent application EP14/867,063.1, dated Jan. 9, 2020, 2 pages.
Claims (2nd auxiliary request—markup version) for European patent application EP14/867,063.1, dated Jan. 9, 2020, 2 pages.

(56) References Cited

OTHER PUBLICATIONS

Claims (2nd auxiliary request—clear version) for European patent application EP14/867,063.1, dated Jan. 9, 2020, 2 pages.
Claims (3rd auxiliary request—markup version) for European patent application EP14/867,063.1, dated Jan. 9, 2020, 2 pages.
Claims (3rd auxiliary request—clear version) for European patent application EP14/867,063.1, dated Jan. 9, 2020, 2 pages.
Claims (4th auxiliary request—markup version) for European patent application EP14/867,063.1, dated Jan. 9, 2020, 2 pages.
Claims (4th auxiliary request—clear version) for European patent application EP14/867,063.1, dated Jan. 9, 2020, 2 pages.
Claims (main request—markup version) for European patent application EP14/867,063.1, dated Jan. 9, 2020, 2 pages.
Claims (main request—clear version) for European patent application EP14/867,063.1, dated Jan. 9, 2020, 2 pages.
Communication pursuant to Article 94(3) EPC for European patent application EP14/867,063.1, dated Feb. 23, 2018, 7 pages.
Communication pursuant to Article 94(3) EPC for European patent application EP14/867,063.1, dated Oct. 12, 2018, 5 pages.
Communication under Rule 71(3) EPC for European patent application EP14/867,063.1, dated Mar. 16, 2020, 80 pages.
Moreira et al., "Cy3 and Cy5 dyes attached to oligonucleotide terminus stabilize DNA duplexes: Predictive thermodynamic model," Biophysical Chemistry, vol. 198, Mar. 2015, p. 36-44. doi.org/10.1016/j.bpc.2015.01.001.
Spiriti et al., "Cy3-DNA Stacking Interactions Strongly Depend on the Identity of the Terminal Basepair," Biophys J. Feb. 16, 2011, 100(4): 1049-1057.

\* cited by examiner

LUMINOPHORE-LABELED MOLECULES COUPLED WITH PARTICLES FOR MICROARRAY-BASED ASSAYS

CROSS-REFERENCE TO RELATED APPLICATIONS

The present application is a divisional application of and claims priority to Non Provisional U.S. application Ser. No. 15/100,970 filed Jun. 1, 2016 and titled Luminophore-Labeled Molecules Coupled with Particles for Microarray-Based Assays, which claims priority benefit to Chinese Patent Application No. 201310651906.5, filed on Dec. 5, 2013, published as CN103760355 A on Apr. 30, 2014, the contents of the above applications are incorporated by reference herein in their entireties for all purposes.

TECHNICAL FIELD

In certain aspects, the present disclosure relates to methods for labeling target molecules for detection using a microarray chip. For example, the target molecules can be nucleic acid molecules coupled to a particle. In particular, the present disclosure relates to microarray-based methods, compositions, and kits for analyzing molecular interactions, e.g., multiplexed genetic analysis of nucleic acid fragments, for diagnosis of clinical samples and disease-associated testing.

Submission Of Sequence Listing On ASCII Text File

The content of the following submission on ASCII text file is incorporated herein by reference in its entirety: a computer readable form (CRF) of the Sequence Listing (file name: 4565-2008210_US16197318_SeqList_ST25, date recorded: Mar. 12, 2019, size: 6,587 bytes).

BACKGROUND

In recently years, microarray technologies enable the evaluation of up to tens of thousands of molecular interactions simultaneously in a high-throughput manner. DNA microarray-based assays have been widely used, including the applications for gene expression analysis, genotyping for mutations, single nucleotide polymorphisms (SNPs), and short tandem repeats (STRs), with regard to drug discovery, disease diagnostics, and forensic purpose (Heller, Ann Rev Biomed Eng (2002) 4: 129-153; Stoughton, Ann Rev Biochem (2005) 74: 53-82; Hoheisel, Nat Rev Genet (2006) 7: 200-210). Pre-determined specific oligonucleotide probes immobilized on microarray can serve as a de-multiplexing tool to sort spatially the products from parallel reactions performed in solution (Zhu et al., Antimicrob Agents Chemother (2007) 51: 3707-3713), and even can be more general ones, e.g., the designed and optimized artificial tags or their complementary sequences employed in the universal microarray (Gerrey et al., J Mol Biol (1999) 292: 251-262; Li et al., Hum Mutat (2008) 29: 306-314). Combined with the multiplex PCR method, microarray-based assays for SNPs and gene mutations, such as deletions, insertions, and indels, thus can be carried out in routine genetic and diagnostic laboratories.

Meanwhile, protein and chemical microarrays have emerged as two important tools in the field of proteomics (Xu and Lam, J Biomed Biotechnol (2003) 5: 257-266). Specific proteins, antibodies, small molecule compounds, peptides, and carbohydrates can now be immobilized on solid surfaces to form microarrays, just like DNA microarrays. These arrays of molecules can then be probed with simple composition of molecules or complex analytes.

Interactions between the analytes and the immobilized array of molecules are evaluated with a number of different detection systems. Typically, commercial use of microarrays employs optical detection with fluorescent, chemiluminescent or enzyme labels, electrochemical detection with enzymes, ferrocene or other electroactive labels, as well as label-free detection based on surface plasmon resonance or microgravimetric techniques (Sassolas et al., Chem Rev (2008) 108: 109-139). To further simplify the assay protocol and reduce the reliance on related equipment, magnetic bead labeling was employed so that assay results could be photographed with a charge-coupled device (CCD) assisted camera or viewed under low magnification microscope (Guo et al., J Anal Sci (2007) 23: 1-4; Li et al., supra; Shlyapnikov et al., Anal Biochem (2010) 399: 125-131), and cross-reactive contacts or unspecific bonds even can be quickly eliminated by applying magnetic field or shear flow (Mulvaney et al., Anal Biochem (2009) 392: 139-144). The detection of microarray-hybridized DNA with magnetic beads thus opens a new way to routine hybridization assays which do not require precise measurements of DNA concentration in solution.

Typically, a fluorescent marker is used to label each target molecule for it to be detected within a plurality of molecules. In these cases, the primers in the PCR reaction often need to be modified by chemical or fluorescent modifications for each target molecule, which can lead to high cost and inhibition of the PCR reaction. There is therefore a need for methods, compositions, and kits for labeling target molecules in a microarray assay that address the above issues and related needs.

SUMMARY

In one aspect, disclosed herein is a method of labeling a plurality of target molecules with a luminophore for detecting the target molecules using a microarray. In some embodiments, the method comprises: coupling each target molecule of a plurality of target molecules to a particle to form a target-particle complex, wherein each target molecule comprises a modification moiety and the particle comprises a plurality of functional moieties, wherein each target molecule is coupled to the particle via interaction between the modification moiety and the functional moiety, and wherein each target molecule comprises a target portion and a portion capable of specific binding to a probe molecule immobilized on a microarray, wherein the microarray comprises a plurality of immobilized probe molecules; and providing a luminophore on the target-particle complex, thereby directly or indirectly labeling the plurality of target molecules with the luminophore. In particular embodiments, the providing step comprises: labeling a subset of the plurality of target molecules with the luminophore, and incubating the plurality of target molecules with the particle, whereby the plurality of target molecules are coupled to the particle, wherein the target-particle complex comprises target molecule(s) labeled with the luminophore and target molecule(s) not labeled with the luminophore; and/or labeling a subset of the functional moieties of the particle with the luminophore, and incubating the luminophore-labeled particle with the plurality of target molecules, whereby the plurality of target molecules are coupled to the particle; and/or introducing the luminophore into or onto the particle to label the particle, and incubating the luminophore-labeled particle with the plurality of target molecules, whereby the plurality of target molecules are coupled to the particle; and/or providing a labeling molecule comprising: (1) the luminophore, and (2) the modification moiety capable of interacting with the functional moiety of the particle, wherein the labeling molecule does not bind to the immobilized probe molecule on the microarray, and incubating the labeling molecule with the plurality of target molecules and the particle, whereby the labeling molecule and the plurality of target molecules are coupled to the particle; and/or providing a binding molecule comprising the luminophore, wherein the binding molecule is capable of specific binding to a subset of the plurality of target molecules, and wherein the binding molecule does not bind to the immobilized probe molecule on the microarray or directly to the particle, and incubating the binding molecule with the plurality of target molecules and the particle, whereby the plurality of target molecules are coupled to the particle.

In another aspect, the present disclosure provides a method of labeling a target molecule with a luminophore for detecting the target molecule using a microarray, the method comprising: coupling a target molecule to a particle to form a target-particle complex, wherein the target molecule comprises a modification moiety and the particle comprises a functional moiety, wherein the target molecule is coupled to the particle via interaction between the modification moiety and the functional moiety, and wherein the target molecule comprises a target portion and a portion capable of specific binding to a probe molecule immobilized on a microarray; and providing a luminophore on the target-particle complex, thereby directly or indirectly labeling the target molecule with the luminophore. In one aspect, the target molecule comprises a plurality of target molecules, and the microarray comprises a plurality of immobilized probe molecules. In another aspect, the particle comprises a plurality of functional moieties, each of which is capable of interacting with the modification moiety of the target molecule, and a plurality of target molecules are coupled to the particle.

In any of the preceding embodiments, each of the plurality of target molecules can comprise a modification moiety capable of interacting with the functional moiety of the particle. In some aspects, the portion of the target molecule capable of specific binding to the immobilized probe molecule comprises a nucleotide sequence.

In any of the preceding embodiments, the method can further comprise a step of detecting the target molecule using the microarray. In one aspect, the detecting step comprises measuring luminescence of the target-particle complex, wherein the complex is immobilized on the microarray via specific binding of the target molecule to the immobilized probe molecule.

In some embodiments, the providing step comprises labeling a subset of the plurality of target molecules with the luminophore, and incubating the plurality of target molecules with the particle, whereby the plurality of target molecules are coupled to the particle, wherein the target-particle complex comprises target molecule(s) labeled with the luminophore and target molecule(s) not labeled with the luminophore, whereby the plurality of target molecules are directly or indirectly labeled with the luminophore.

In one embodiment, the providing step comprises labeling a subset of the functional moieties of the particle with the luminophore, and incubating the luminophore-labeled particle with the plurality of target molecules, whereby the plurality of target molecules are coupled to the particle, whereby the plurality of target molecules are indirectly labeled with the luminophore.

In some embodiments, the providing step comprises introducing the luminophore into or onto the particle to label the particle, and incubating the luminophore-labeled particle with the plurality of target molecules, whereby the plurality of target molecules are coupled to the particle, whereby the plurality of target molecules are indirectly labeled with the luminophore.

In other embodiments, the providing step comprises providing a labeling molecule comprising: (1) the luminophore, and (2) the modification moiety capable of interacting with the functional moiety of the particle, wherein the labeling molecule does not bind to the immobilized probe molecule on the microarray, and incubating the labeling molecule with the plurality of target molecules and the particle, whereby the labeling molecule and the plurality of target molecules are coupled to the particle, whereby the plurality of target molecules are indirectly labeled with the luminophore. In one aspect, the labeling molecule does not contain the target portion of the target molecule. In another aspect, the labeling molecule does not bind to the plurality of target molecules.

In still other embodiments, the providing step comprises providing a binding molecule comprising the luminophore, wherein the binding molecule is capable of specific binding to a subset of the plurality of target molecules, and wherein the binding molecule does not bind to the immobilized probe molecule on the microarray or directly to the particle, and incubating the binding molecule with the plurality of target molecules and the particle, whereby the plurality of target molecules are coupled to the particle, whereby the plurality of target molecules are indirectly labeled with the luminophore.

In any of the preceding embodiments, the target molecule can comprise a polynucleotide, a polypeptide, an antibody, a small molecule compound, a peptide, a carbohydrate, or a combination thereof. In one aspect, the target molecule is a polynucleotide enriched by an amplification reaction such as PCR.

In any of the preceding embodiments, the functional moiety can be selected from the group consisting of a chemical group, a polynucleotide, a polypeptide, an antibody, a small molecule compound, a peptide, and a carbohydrate. In one aspect, the chemical group is an aldehyde, hydroxyl, carboxyl, ester, amine, sulfo, or sulfhydryl group.

In any of the preceding embodiments, the functional moiety can be streptavidin, neutravidin, or avidin. In any of the preceding embodiments, the luminophore can be a fluorophore, a phosphorescent moiety, or a chromophore. In any of the preceding embodiments, the modification moiety can be biotin, digoxin, digoxigenin, a polynucleotide, a poly-dA, apoly-dT, a protein, a polypeptide, or a carbohydrate. In any of the preceding embodiments, the luminophore can be a quantum dot, a luminescent protein, a green fluorescent protein (GFP), or a small molecule fluorescent dye. In some embodiments, the small molecule fluorescent dye is selected from the group consisting of: a xanthene derivative, fluorescein, rhodamine, Oregon green, eosin, texas red; a cyanine derivative, cyanine, indocarbocyanine, oxacarbocyanine, thiacarbocyanine, merocyanine; a naphthalene derivative, a dansyl derivative, a prodan derivative, a dansyl and prodan derivative; a coumarin derivative; a thiadiazole derivative; an oxadiazole derivative, pyridyloxazole, nitrobenzoxadiazole, benzoxadiazole; a pyrene derivative, cascade blue; BODIPY (Invitrogen); an oxazine derivative, Nile red, Nile blue, cresyl violet, oxazine 170; an acridine derivative, proflavin, acridine orange, acridine yellow; an arylmethine derivative, auramine, crystal violet, malachite green; a CF dye (Biotium), an Alexa Fluor dye (Invitrogen), Atto and Tracy (Sigma), a Tetrapyrrole derivative, porphin, phtalocyanine, bilirubin, cascade yellow, azure B, acridine orange, DAPI, Hoechst 33258, lucifer yellow, piroxicam, quinine, anthraqinone, squarylium, and oligophenylenes.

In any of the preceding embodiments, the luminophore can be a compound of a transition metal or a rare earth compound. In any of the preceding embodiments, the luminophore can be a food coloring agent, a fabric dye, lycopene, n-carotene, an anthocyanin, chlorophyll, hemoglobin, hemocyanin, or a mineral. In one aspect, the fabric dye is an azo compound. In one aspect, the mineral is malachite or amethyst.

In any of the preceding embodiments, the particle can be a microparticle. In any of the preceding embodiments, the particle diameter can be between about 0.1 micrometers and about 10 micrometers, about 0.1 micrometers and about 0.5 micrometers, about 0.5 micrometers and about 1 micrometer, about 1 micrometer and about 2 micrometers, about 2 micrometers and about 4 micrometers, about 4 micrometers and about 6 micrometers, about 6 micrometers and about 8 micrometers, or about 8 micrometers and about 10 micrometers. In some embodiments, the particle diameter is less than about 0.1 micrometers, or more than about 10 micrometers. In some embodiments, the particle is a magnetic particle or a paramagnetic particle. In some aspects, the particle is a paramagnetic microsphere.

In any of the preceding embodiments, the immobilized probe molecule on the microarray can comprise a polynucleotide, a protein, a polypeptide, or a carbohydrate. In some aspects, the microarray comprises a substrate comprising silicon, glass, plastic, hydrogel, agarose, nitrocellulose, nylon, or a combination thereof.

In another aspect, provided herein is a method of detecting a target molecule using a microarray, the method comprising: labeling a target molecule with a luminophore according to any of the preceding embodiments; incubating the target molecule and the particle with the microarray, wherein the target-particle complex is immobilized on the microarray via specific binding of the target molecule to the immobilized probe molecule; and measuring luminescence of the immobilized target-particle complex, wherein the luminescence indicates the absence, presence, and/or amount of the target molecule. In one aspect, the method further comprises identifying the target portion of the target molecule based on the immobilized probe molecule on the microarray.

In any of the preceding embodiments, the target molecule can be associated with a disease caused by an infectious or pathogenic agent selected from the group consisting of a fungus, a bacterium, a mycoplasma, a rickettsia, a chlamydia, a virus, and a protozoa. In any of the preceding embodiments, the target molecule can be associated with a sexually transmitted disease, cancer, cerebrovascular disease, heart disease, respiratory disease, coronary heart disease, diabetes, hypertension, Alzheimer's disease, neurodegenerative disease, chronic obstructive pulmonary disease, autoimmune disease, cystic fibrosis, spinal muscular atrophy, thalassemia (such as alpha-thalassemia, beta-thalassemia, and delta-thalassemia), phenylalanine hydroxylase deficiency, Duchenne muscular dystrophy, or hereditary hearing loss.

In any of the preceding embodiments, the probe molecule can comprise a polynucleotide, a polypeptide, an antibody, a small molecule compound, a peptide, a carbohydrate, or a combination thereof. In any of the preceding embodiments, the microarray can comprise at least two probe molecules, for example, at least about 5, about 10, about 50, about 100, about 1,000, about $10^4$, about $10^5$, about $10^5$, about $10^6$, about $10^7$, about $10^8$, about $10^9$, about $10^{10}$, or more than about $10^{10}$ probe molecules.

In any of the preceding embodiments, the microarray can be fabricated using a technology selected from the group consisting of printing with a fine-pointed pin, photolithography using a pre-made mask, photolithography using a dynamic micromirror device, ink-jet printing, microcontact printing, and electrochemistry on a microelectrode array. In any of the preceding embodiments, a spot on the microarray can range from about 1 micrometer to about 5000 micrometers in diameter. In some aspects, the spot can range from about 1 micrometer to about 10 micrometers, about 10 micrometers to about 100 micrometers, about 100 micrometers to about 500 micrometers, about 500 micrometers to about 1000 micrometers, about 1000 micrometers to about 2500 micrometers, or about 2500 micrometers to about 5000 micrometers in diameter.

In any of the preceding embodiments, the probe molecule can be attached to the microarray by in situ synthesis, nonspecific adsorption, specific binding, nonspecific chemical ligation, chemoselective ligation, or covalent binding. In any of the preceding embodiments, the interaction between the target molecule and the probe molecule can be a non-covalent, reversible covalent or irreversible covalent interaction.

In any of the preceding embodiments, the efficiency and/or efficacy of the interaction between the target molecule and the probe molecule can be enhanced by an external force. In some aspects, the external force is a magnetic force, a dielectrophoretic force, a mechanical force, or a combination thereof.

In any of the preceding embodiments, the target molecule can be subject to an in vitro manipulation, for example, laser treatment, ultrasonication treatment, heat treatment, microwave treatment, piezoelectricity treatment, electrophoresis, dielectrophoresis, solid phase adhesion, filtration, fluidic stress, enzymatic digestion, PCR amplification, reverse-transcription, reverse-transcription PCR amplification, allele-specific PCR (ASPCR), single-base extension (SBE), allele specific primer extension (ASPE), restriction enzyme digestion, strand displacement amplification (SDA), transcription mediated amplification (TMA), ligase chain reaction (LCR), nucleic acid sequence based amplification (NASBA), primer extension, rolling circle amplification (RCA), self sustained sequence replication (3SR), the use of Q Beta replicase, nick translation, or loop-mediated isothermal amplification (LAMP), or any combination of the in vitro manipulations disclosed herein.

In any of the preceding embodiments, the target molecule can comprise a double-stranded polynucleotide and/or a single stranded polynucleotide. In one aspect, the target molecules is a double-stranded polynucleotide and is denatured to become single-stranded by a chemical reaction, an enzyme, heating, or a combination thereof, before or after coupling to the particle. In one aspect, the enzyme is an exonuclease, a Uracil-N-glycosylase, or a combination thereof. In one aspect, the chemical reaction uses urea, formamide, methanol, ethanol, sodium hydroxide, or a combination thereof. In another aspect, the double-stranded target polynucleotide is denatured at an appropriate temperature from about 30° C. to about 95° C., about 30° C. to about 35° C., about 35° C. to about 40° C., about 40° C. to about 45° C., about 45° C. to about 50° C., about 50° C. to about 55° C., about 55° C. to about 60° C., about 60° C. to about 65° C., about 65° C. to about 70° C., about 70° C. to about 75° C., about 75° C. to about 80° C., about 80° C. to about 85° C., about 85° C. to about 90° C., or about 90° C. to about 95° C.

In any of the preceding embodiments, the target molecule can be a polynucleotide and can be coupled to the particle through a streptavidin/biotin interaction, a neutravidin/biotin interaction, an avidin/biotin interaction, or a poly-dT/dA interaction.

In any of the preceding embodiments, the target molecule can comprise a universal tag sequence. In one aspect, the target molecule is a polynucleotide of a species, and wherein the universal tag sequence has low homology to the genomic DNA of the species. In another aspect, the tag sequence has no hair-pin structure. In any of the preceding embodiments, the tag sequence can be a single stranded oligonucleotide or modified analog.

In any of the preceding embodiments, the tag sequence can be a locked nucleic acid (LNA), a Zip nucleic acid (ZNA), or a peptide nucleic acid (PNA). In any of the preceding embodiments, at least two different universal tag sequences can be used. In one aspect, the $T_m$ difference between different tag sequences equals or is less than about 5° C. In some aspects, the $T_m$ difference is about 0.1° C., about 0.5° C., about 1° C., about 1.5° C., about 2° C., about 2.5° C., about 3° C., about 3.5° C., about 4° C., about 4.5° C., or about 5° C. In another aspect, different tag sequences have no cross-hybridization among themselves.

In any of the preceding embodiments, the tag sequence can be introduced to the target molecule during an in vitro manipulation.

In any of the preceding embodiments, the method can further comprise detecting the target molecule by a microarray scanning device, an ordinary image-capturing device, or a naked eye. In some aspects, the microarray scanning device employs optical detection with a fluorescent label, a chemiluminescent label, a phosphorescent label, or a chromophore label. In one embodiment, the microarray scanning device employs one or more detection methods based on surface plasmon resonance, magnetic force, giant magnetoresistance, or microgravimetric technique. In one embodiment, the ordinary image-capturing device is a flatbed scanner, a camera, or a portable device. In one aspect, the camera is with or without the assistance of a lens, a magnifier, or a microscope. In one aspect, the portable device is a camera on a mobile phone or a laptop computer with or without the assistance of a lens, a magnifier, or a microscope.

In any of the preceding embodiments, the target molecule can be a single stranded polynucleotide. In one aspect, the complementary strand of the target polynucleotide is labeled.

In any of the preceding embodiments, the target molecule can be associated with a genetic information, for example, a substitution, an insertion, a deletion, an indel, or any combination thereof. In one aspect, the genetic information is a single nucleotide polymorphism (SNP).

In any of the preceding embodiments, the genetic information can be associated with a disease caused by an infectious or pathogenic agent selected from the group consisting of a fungus, a bacterium, a mycoplasma, a rickettsia, a chlamydia, a virus, and a protozoa. In any of the preceding embodiments, the genetic information can be associated with a sexually transmitted disease, cancer, cerebrovascular disease, heart disease, respiratory disease, coronary heart disease, diabetes, hypertension, Alzheimer's disease, neurodegenerative disease, chronic obstructive pulmonary disease, autoimmune disease, cystic fibrosis, spinal muscular atrophy, beta thalassemia, phenylalanine hydroxylase deficiency, Duchenne muscular dystrophy, or hereditary hearing loss. In one aspect, the genetic information is associated with hereditary hearing loss. In some embodiments, the genetic information is within a target gene of GJB2 (Cx26), GJB3 (Cx31), SLC26A4 (PDS), 12S rRNA (MTRNR1), or a β-globin gene such as HBB. In some aspects, the genetic information in GJB2 is selected from the group consisting of c.35delG, c.176_191del16, c.235delC, and c.299_300delAT. In one aspect, the genetic information in SLC26A4 is selected from the group consisting of c.2168A>G, IVS7-2A>G (c.919-2A>G), c.1229C>T, c.1975G>C, c.1174A>T, c.1226G>A, c.2027T>A, and IVS15+5G>A. In one aspect, the genetic information in GJB3 (Cx31) is c.538 C>T. In another aspect, the genetic information in 12S rRNA is selected from the group consisting of m.1494C>T and m.1555A>G. In one aspect, the genetic information is associated with beta thalassemia. In some embodiments, the genetic information is within a target gene of HBB. In some aspects, the genetic information in HBB is selected from the group consisting of c.-82C>A, c.-80T>C, c.-79A>G, c.-78A>G, c.-11_8delAAAC, c.79G>A, c.91A>G, c.92+1G>T, c.92+5G>C, c.315+5G>C, c.316-197C>T, c.2T>G, c.45_46insG, c.84_85insC, c.52A>T, c.113G>A, c.126_129delCTTT, c.130G>T, and c.216_217insA.

In any of the preceding embodiments, ASPCR can be used to amplify the genetic information. In one aspect, the set of primers for the ASPCR comprises at least two allele-specific primers and one common primer. In one embodiment, the allele-specific primers and the common primer have a sequence as set forth in Table 2. In another embodiment, the allele-specific primers terminate at the SNP/mutation locus.

In any of the preceding embodiments, the allele-specific primers can further comprise an artificial mismatch to the corresponding target sequence. In any of the preceding embodiments, the allele-specific primers can comprise a natural nucleotide or analog thereof. In any of the preceding embodiments, the allele-specific primers can comprise a tag sequence.

In any of the preceding embodiments, the ASPCR can use a DNA polymerase without the 3' to 5' exonuclease activity. In any of the preceding embodiments, genetic information of at least two genetic loci can be detected. In one aspect, multiplex PCR is used to amplify the genetic information of the at least two genetic loci.

In any of the preceding embodiments, the genetic material for ASPCR can be isolated from tissues, cells, body fluids, hair, nail and ejaculate, including saliva sample, sputum sample, sperm sample, oocyte sample, zygote sample, lymph sample, blood sample, interstitial fluid sample, urine sample, buccal swab sample, chewing gum sample, cigarette butt sample, envelope sample, stamp sample, prenatal sample, or dried blood spot sample.

In one aspect, disclosed herein is a composition comprising: a plurality of target molecules, a subset of which is labeled with a luminophore, wherein each of the target molecules comprises a modification moiety and a portion capable of specific binding to an immobilized probe molecule on a microarray; and a particle comprising a plurality of functional moieties capable of interacting with the modification moieties of the target molecules, wherein the plurality of target molecules are coupled to the particle via interaction between the modification moieties and the functional moieties, and wherein the plurality of target molecules are directly or indirectly labeled with the luminophore.

In another aspect, disclosed herein is a composition comprising: a plurality of target molecules, wherein each of the target molecules comprises a modification moiety and a portion capable of specific binding to an immobilized probe molecule on a microarray; and a particle comprising a plurality of functional moieties capable of interacting with the modification moieties of the target molecules, a subset of which functional moieties of the particle is labeled with a luminophore, wherein the plurality of target molecules are coupled to the particle via interaction between the modification moieties and the functional moieties, and wherein the plurality of target molecules are indirectly labeled with the luminophore.

In still another aspect, disclosed herein is a composition comprising: a plurality of target molecules, wherein each of the target molecules comprises a modification moiety and a portion capable of specific binding to an immobilized probe molecule on a microarray; and a particle comprising a plurality of functional moieties capable of interacting with the modification moieties of the target molecules, wherein the particle comprises a luminophore introduced therein, wherein the plurality of target molecules are coupled to the particle via interaction between the modification moieties and the functional moieties, and wherein the plurality of target molecules are indirectly labeled with the luminophore.

In still another aspect, disclosed herein is a composition comprising: a plurality of target molecules, wherein each of the target molecules comprises a modification moiety and a portion capable of specific binding to an immobilized probe molecule on a microarray; a particle comprising a plurality of functional moieties capable of interacting with the modification moieties of the target molecules; and a labeling molecule comprising a luminophore, wherein the labeling molecule is capable of interacting with the functional moiety of the particle, wherein the labeling molecule does not bind to the immobilized probe molecule on the microarray, wherein the labeling molecule and the plurality of target molecules are coupled to the particle via interaction between the modification moieties and the functional moieties, and wherein the plurality of target molecules are indirectly labeled with the luminophore. In one embodiment, the labeling molecule does not bind to the plurality of target molecules.

In one other aspect, disclosed herein is a composition comprising: a plurality of target molecules, wherein each of the target molecules comprises a modification moiety and a portion capable of specific binding to an immobilized probe molecule on a microarray; a particle comprising a plurality of functional moieties capable of interacting with the modification moieties of the target molecules; and a binding molecule comprising a luminophore, wherein the binding molecule is capable of specific binding to a subset of the plurality of target molecules, and wherein the binding molecule does not bind to the immobilized probe molecule on the microarray or directly to the particle, wherein the plurality of target molecules are coupled to the particle via interaction between the modification moieties and the functional moieties, and wherein the plurality of target molecules are indirectly labeled with the luminophore.

In any of the preceding embodiments, the probe molecule can be selected from the group consisting of a polynucleotide, a polypeptide, an antibody, a small molecule compound, a peptide and a carbohydrate. In some embodiments, the particle is a microparticle. In some aspects, the microparticle is a paramagnetic microsphere. In some embodiments, the microparticle has a diameter from about 0.1 micrometers to about 10 micrometers. In some embodiments, the particle diameter can be between about 0.1 micrometers and about 0.5 micrometers, about 0.5 micrometers and about 1 micrometer, about 1 micrometer and about 2 micrometers, about 2 micrometers and about 4 micrometers, about 4 micrometers and about 6 micrometers, about 6 micrometers and about 8 micrometers, or about 8 micrometers and about 10 micrometers. In some embodiments, the particle diameter is less than about 0.1 micrometers, or more than about 10 micrometers.

In one aspect, disclosed herein is a kit for labeling a target molecule with a luminophore for detecting the target molecule using a microarray, the kit comprising: a luminophore; means for labeling a subset of a plurality of target molecules with the luminophore; a particle comprising a plurality of functional moieties, each of the functional moieties capable of interacting with a modification moiety of a target molecule; and a plurality of probe molecules immobilized on a microarray, each immobilized probe molecule capable of specific binding to a target molecule.

In another aspect, disclosed herein is a kit for labeling a target molecule with a luminophore for detecting the target molecule using a microarray, the kit comprising: a luminophore; a particle comprising a plurality of functional moieties, each of the functional moieties capable of interacting with a modification moiety of a target molecule; means for labeling a subset of the plurality of functional moieties with the luminophore; and a plurality of probe molecules immobilized on a microarray, each immobilized probe molecule capable of specific binding to a target molecule.

In still another aspect, disclosed herein is a kit for labeling a target molecule with a luminophore for detecting the target molecule using a microarray, the kit comprising: a luminophore; a particle comprising a plurality of functional moieties, each of the functional moieties capable of interacting with a modification moiety of a target molecule; means for introducing the luminophore into or onto the particle; and a plurality of probe molecules immobilized on a microarray, each immobilized probe molecule capable of specific binding to a target molecule.

In one other aspect, disclosed herein is a kit for labeling a target molecule with a luminophore for detecting the target molecule using a microarray, the kit comprising: a luminophore; a particle comprising a plurality of functional moieties, each of the functional moieties capable of interacting with a modification moiety of a target molecule; a labeling molecule comprising the modification moiety capable of interacting with the functional moiety of the particle; means for labeling the labeling molecule with the luminophore; and a plurality of probe molecules immobilized on a microarray, each immobilized probe molecule capable of specific binding to a target molecule. In one aspect, the labeling molecule does not bind to the immobilized probe molecules on the microarray.

In yet another aspect, a kit is provided herein for labeling a target molecule with a luminophore for detecting the target molecule using a microarray, the kit comprising: a luminophore; a binding molecule capable of specific binding to a subset of a plurality of target molecules; a particle comprising a plurality of functional moieties, each of the functional moieties capable of interacting with a modification moiety of the target molecules; means for labeling the binding molecule with the luminophore; and a plurality of probe molecules immobilized on a microarray, each immobilized probe molecule capable of specific binding to a target molecule. In one embodiment, the binding molecule does not bind to the immobilized probe molecules on the microarray or directly to the particle.

In any of the preceding embodiments, the kit can further comprise a primer comprising a sequence as set forth in Table 2 without the Tag sequence, the biotinylated universal primer sequence at the 5'-terminus, or the Cy3 label, which primer is not a full-length cDNA or a full-length genomic DNA. In any of the preceding embodiments, the kit can further comprise a primer comprising the sequence as set forth in Table 2.

In any of the preceding embodiments, the kit can further comprise a set of primers for ASPCR amplification of a genetic information comprising two allele-specific primers and a common primer as set forth in Table 2.

In any of the preceding embodiments, the kit can further comprise a universal tag array comprising at least two of the tag sequences as set forth in Table 1.

In any of the preceding embodiments, the particle can be a microparticle or a paramagnetic microsphere. In any of the preceding embodiments, the microparticle can have a diameter from about 0.1 micrometers to about 10 micrometers.

In any of the preceding embodiments, the functional group can comprise a chemical group, a polynucleotide, a polypeptide, an antibody, a small molecule compound, a peptide, a carbohydrate, or a combination thereof. In one aspect, the chemical group is an aldehyde, hydroxyl, carboxyl, ester, amine, sulfo, or sulthydryl group. In another aspect, the polypeptide is streptavidin, neutravidin, or avidin. In yet another aspect, the polynucleotide is poly-dT or poly-dA.

BRIEF DESCRIPTION OF THE DRAWINGS

FIG. 1A shows arrangement of the tags as shown in Table 1 on the array. FIG. 1B shows arrangement of the wild-type probes of polymorphism loci (W) and the mutant probes of polymorphism loci (M) on the array.

DETAILED DESCRIPTION

Figure 1A:
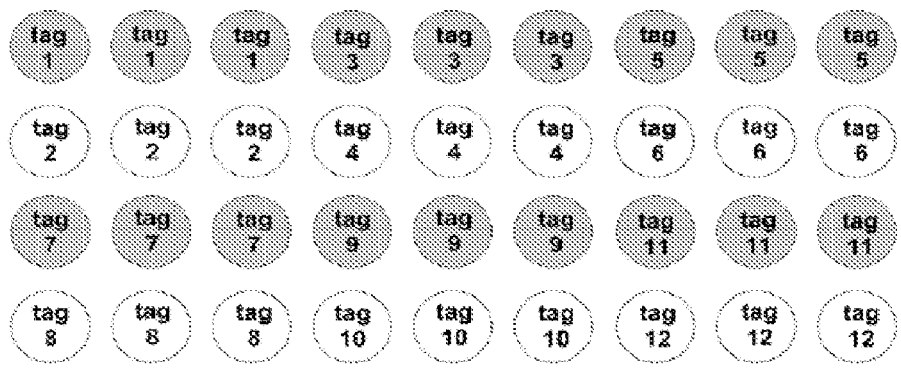
FIGS. 1A and 1B together is a schematic for the layout of a universal tag array for multiplexing, according to one aspect of the present disclosure.

In some aspects, the present disclosure provides a method that combines microarray-based assays with particles and luminophore-labeled target molecules. In some embodiments, the method combines microarray-based assays with particles, through enriching luminophore-labeled target nucleic acid fragments, and coupling particles to microarray spots through target-probe hybridization. In some embodiments, the method combines microarray-based assays with particles, through enriching luminophore-labeled double-stranded or single-stranded nucleic acid fragments, and coupling particles to microarray spots through target-probe hybridization. In some aspect, a method disclosed herein further comprises a step of de-multiplexing.

In one aspect, a microarray-based assay is provided, which is used for analyzing molecular interactions, including interactions between polynucleotides, polypeptides, antibodies, small molecule compounds, peptides and carbohydrates. In certain embodiments, the method disclosed herein comprises labeling a target molecule with a luminophore. In some embodiments, the method further comprises coupling the target molecule to a particle, and binding to a probe molecule on microarray. In particular, multiplexed genetic analysis of nucleic acid fragments can be implemented. Specific genes, single nucleotide polymorphisms or gene mutations, such as deletions, insertions, and indels, can be identified. In one aspect, this technology enables the detection and interpretation of molecular interactions in an efficient way with high sensitivity.

In one aspect, luminophores improve the detection of target-probe binding in microarray-based assays because they exhibit variations in signal intensity or emission spectra resulting from the binding of target-probe molecular complex. In some embodiments, luminophore-labeling is integrated with magnetic beads, facilitating the process of microarray-based assays. Luminophore-labeled molecules can be coupled to magnetic beads, each of which assembles a large amount of luminophores at the same time, yielding high intensity of luminescence. High sensitivity detection of molecular interaction is thus achieved.

In some aspects, the present disclosure provides methods, compositions, and kits for improving both sensitivity and specificity of microarray-based assays, concerning with the detection of various SNPs and gene mutations, particularly in clinical settings. Typically, hybridization of labeled nucleic acid targets with surface-immobilized oligonucleotide probes is the central event in the detection of nucleic acids on microarrays (Riccelli et al., Nucleic Acids Res (2001) 29: 996-1004). In some cases, only one of the two strands of DNA products is available to hybridize with these probes while the other one competes with the probes for the targets, acting as a severe interfering factor. Therefore, in some aspects, single-stranded DNA (ssDNA) is enriched, and asymmetric polymerase chain reaction (PCR) is used. In another aspect, a one-step asymmetric PCR without purification process is also used, providing enhanced sensitivity and specificity (Gao et al., Anal Lett (2003) 33: 2849-2863; Zhu et al., supra; Li et al., supra).

In some aspects, microspheres, preferably paramagnetic microspheres are used, due to their easy handling and good biocompatibility, which can be further improved with the concern of sensitivity (Gao et al., supra). Through capturing double-stranded DNA fragments with microspheres and removing the unwanted strands by denaturation methods, the yielded ssDNA products can be hybridized with microarrays. In one aspect, the purer and more abundance the ssDNA products can be made, the better sensitivity is expected. As the common symmetric PCR has its properties of much higher amplification efficiency and easier design of multiplexing compared with asymmetric PCR, in one aspect, the use of symmetric PCR and use of ssDNAs can be combined.

Besides ensuring the high sensitivity and specificity, in another aspect, combining microarray-based assays with particles and luminophore-labeling facilitates the examination of assay results with appropriate devices. In some aspects, the combination method is used for the detection of SNP/mutation related to hereditary hearing loss and/or beta-thalassemia, for multiplexed genetic analysis, or for diagnosis of clinical samples and disease-associated genetic testing.

In some aspects, the present disclosure provides the following advantages:

1. By directly or indirectly labeling the luminophores to the target molecules, the present disclosure not only greatly reduces the cost of fluorescence detection, but also avoids the PCR inhibition derived from traditional fluorescence labeling molecules.

2. The luminophores are labeled to one kind of target molecule (e.g., a subset) in a plurality of modified target molecules, thereby achieving the goal of reducing the cost of fluorescence labeling of the target, the fluorescence labeling of the primers, and the inhibition of PCR amplification efficiency to a large extent.

3. When the luminophores are introduced into the microparticles, or labeled to the functional groups that are coated on the surface of the microparticles, or labeled to a binding molecule, or labeled to a labeling molecule, the method significantly reduces the inhibition of PCR amplification. In another aspect, the luminophore amount required in the present disclosure is only about 10% of that required when each target molecule is labeled individually. It should be noted that the labeling methods disclosed herein can be combined in any suitable manner, to further increase the labeling efficiency and to reduce inhibition of PCR reactions. For example, luminophores can be simultaneously introduced into the microparticle and labeled to the functional groups on the surface of the microparticle, and/or labeled to a binding molecule, and/or labeled to a labeling molecule.

4. When the binding molecule is labeled with a luminophore, the binding molecule does not bind to the modification moiety of the modified target molecule (therefore does not prevent the target molecule from binding to the particle). Because the binding molecules can be made short and they do not bind to the particle, they can efficiently bind to the target molecules such that each particle comprises multiple bound target molecules that are labeled with the luminophore-labeled binding molecules.

A detailed description of one or more embodiments of the claimed subject matter is provided below along with accompanying figures that illustrate the principles of the claimed subject matter. The claimed subject matter is described in connection with such embodiments, but is not limited to any particular embodiment. It is to be understood that the claimed subject matter may be embodied in various forms, and encompasses numerous alternatives, modifications and equivalents. Therefore, specific details disclosed herein are not to be interpreted as limiting, but rather as a basis for the claims and as a representative basis for teaching one skilled in the art to employ the claimed subject matter in virtually any appropriately detailed system, structure, or manner. Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. It should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. For the purpose of clarity, technical material that is known in the technical fields related to the claimed subject matter has not been described in detail so that the claimed subject matter is not unnecessarily obscured.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

All publications, including patent documents, scientific articles and databases, referred to in this application are incorporated by reference in their entireties for all purposes to the same extent as if each individual publication were individually incorporated by reference. If a definition set forth herein is contrary to or otherwise inconsistent with a definition set forth in the patents, patent applications, published applications or other publications that are herein incorporated by reference, the definition set forth herein prevails over the definition that is incorporated herein by reference. Citation of the publications or documents is not intended as an admission that any of them is pertinent prior art, nor does it constitute any admission as to the contents or date of these publications or documents.

All headings are for the convenience of the reader and should not be used to limit the meaning of the text that follows the heading, unless so specified.

The practice of the provided embodiments will employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polypeptide and protein synthesis and modification, polynucleotide synthesis and modification, polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds., *Genome Analysis: A Laboratory Manual Series* (Vols. I-IV) (1999); Weiner, Gabriel, Stephens, Eds., *Genetic Variation: A Laboratory Manual* (2007); Dieffenbach, Dveksler, Eds., *PCR Primer: A Laboratory Manual* (2003); Bowtell and Sambrook, *DNA Microarrays: A Molecular Cloning Manual* (2003); Mount, *Bioinformatics: Sequence and Genome Anazvsis* (2004); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Ausubel et al. eds., *Current Protocols in Molecular Biology* (1987); T. Brown ed., *Essential Molecular Biology* (1991), IRL Press; Goeddel ed., *Gene Expression Technology* (1991), Academic Press; A. Bothwell et al. eds., *Methods for Cloning and Analysis of Eukaryotic Genes* (1990), Bartlett Publ.; M. Kriegler, *Gene Transfer and Expression* (1990), Stockton Press; R. Wu et al. eds., *Recombinant DNA Methodology* (1989), Academic Press; M. McPherson et al., *PCR: A Practical Approach* (1991), *IRL Press* at Oxford University Press; Stryer, *Biochemistry* (4th Ed.) (1995), W. H. Freeman, New York N.Y.; Gait, *Oligonucleotide Synthesis: A Practical Approach* (2002), IRL Press, London; Nelson and Cox, *Lehninger, Principles of Biochemistry* (2000) 3rd Ed., W. H. Freeman Pub., New York, N.Y.; Berg, et al., *Biochemistry* (2002) 5th Ed., W. H. Freeman Pub., New York, N.Y.; D. Weir & C. Blackwell, eds., *Handbook of Experimental Immunology* (1996), Wiley-Blackwell; A. Abbas et al., *Cellular and Molecular Immunology* (1991, 1994), W.B. Saunders Co.; and J. Coligan et at eds., *Current Protocols in Immunology* (1991), all of which are herein incorporated in their entireties by reference for all purposes.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

A. DEFINITIONS

As used herein, the singular forms "a", "an", and "the" include plural references unless indicated otherwise. For example, "a" dimer includes one or more dimers.

The term "molecule" is used herein to refer to any chemical or biochemical structure which includes, but is not limited to, polynucleotides, polypeptides, antibodies, small molecule compounds, peptides, and carbohydrates.

A "target" molecule refers to the molecule to be detected by the methods described in the current disclosure. In the case of a double stranded polynucleotide, the target molecule may refer to either or both of the complementary strands.

The term "luminophore" is used herein to refer to an atom or atomic grouping in a chemical compound that manifests luminescence.

The term "particle" or "microparticle" is meant to refer to small particles, preferred herein in diameter from about 0.01 micrometers to about 1000 micrometers, for example, from about 0.01 micrometers to about 0.1 micrometers, from about 0.1 micrometers to about 0.5 micrometers, from about 0.5 micrometers to about 1 micrometer, from about 1 micrometer to about 5 micrometers, from about 5 micrometers to about 10 micrometers, from about 10 micrometers to about 100 micrometers, from about 100 micrometers to about 500 micrometers, or from about 500 micrometers to about 1000 micrometers. In some embodiments, a "particle" or "microparticle" includes an inherent property (e.g., magnetization, fluorescence and the like) allowing identification of each particle or microparticle as belonging to a specific group. The term "microsphere" is meant to refer to a particle, preferably spherical and usually within the range of from about 0.01 micrometers to about 1000 micrometers, for example, from about 0.01 micrometers to about 0.1 micrometers, from about 0.1 micrometers to about 0.5 micrometers, from about 0.5 micrometers to about 1 micrometer, from about 1 micrometer to about 5 micrometers, from about 5 micrometers to about 10 micrometers, from about 10 micrometers to about 100 micrometers, from about 100 micrometers to about 500 micrometers, or from about 500 micrometers to about 1000 micrometers. In some embodiment, a microsphere may comprise one or more identifying tags (e.g., magnetization, fluorescence and the like) formed together with a polymer, glass, or other matrix, coating or the like. The term "magnetic microsphere" is meant to refer to a particle within the range of from about 0.01 micrometers to about 1000 micrometers (for example, from about 0.01 micrometers to about 0.1 micrometers, from about 0.1 micrometers to about 0.5 micrometers, from about 0.5 micrometers to about 1 micrometer, from about 1 micrometer to about 5 micrometers, from about 5 micrometers to about 10 micrometers, from about 10 micrometers to about 100 micrometers, from about 100 micrometers to about 500 micrometers, or from about 500 micrometers to about 1000 micrometers) including one or more magnetic domains with a polymer, glass, or other matrix, coating or the like. Neither the term "microsphere" or "magnetic microsphere" is meant to exclude shapes other than spherical, and such terms are meant to include other shapes such as globular, flat and the like.

The term "microarray" is used herein to refer to polynucleotide, polypeptide or chemical microarrays. Specific polynucleotides, polypeptides, antibodies, small molecule compounds, peptides, and carbohydrates can be immobilized on solid surfaces to form microarrays.

The term "binding" is used herein to refer to an attractive interaction between two molecules which results in a stable association in which the molecules are in close proximity to each other. Molecular binding can be classified into the following types: non-covalent, reversible covalent and irreversible covalent. Molecules that can participate in molecular binding include polypeptides, polynucleotides, carbohydrates, lipids, and small organic molecules such as pharmaceutical compounds. Polypeptides that form stable complexes with other molecules are often referred to as receptors while their binding partners are called ligands. Polynucleotides can also form stable complex with themselves or others, for example, DNA-protein complex, DNA-DNA complex, DNA-RNA complex.

The term "polypeptide" is used herein to refer to proteins, fragments of proteins, and peptides, whether isolated from natural sources, produced by recombinant techniques, or chemically synthesized. A polypeptide may have one or more modifications, such as a post-translational modification (e.g., glycosylation, etc.) or any other modification (e.g., pegylation, etc.). The polypeptide may contain one or more non-naturally-occurring amino acids (e.g., such as an amino acid with a side chain modification). Polypeptides of the present disclosure may typically comprise at least about 10 amino acids.

The terms "polynucleotide," "oligonucleotide," "nucleic acid" and "nucleic acid molecule" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing normucleotidic backbones, for example, polyamide (e.g., peptide nucleic acid ("PNA")) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. Thus, these terms include, for example, 3'-deoxy-2', 5'-DNA, oligodeoxyribonucleotide N3' to P5' phosphoramidates, 2'-O-alkyl-substituted RNA, hybrids between DNA and RNA or between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

"Nucleic acid probe" and "probe" are used interchangeably and refer to a structure comprising a polynucleotide, as defined above, that contains a nucleic acid sequence that can bind to a corresponding target. The polynucleotide regions of probes may be composed of DNA, and/or RNA, and/or synthetic nucleotide analogs.

As used herein, "complementary or matched" means that two nucleic acid sequences have at least 50% sequence identity. Preferably, the two nucleic acid sequences have at least 60%, 70%, 80%, 90%, 95%, 96%, 97%, 98%, 99% or 100% of sequence identity. "Complementary or matched" also means that two nucleic acid sequences can hybridize under low, middle and/or high stringency condition(s). The percentage of sequence identity or homology is calculated by comparing one to another when aligned to corresponding portions of the reference sequence.

As used herein, "substantially complementary or substantially matched" means that two nucleic acid sequences have at least 90% sequence identity. Preferably, the two nucleic acid sequences have at least 95%, 96%, 97%, 98%, 99% or 100% of sequence identity. Alternatively, "substantially complementary or substantially matched" means that two nucleic acid sequences can hybridize under high stringency condition(s). The percentage of sequence identity or homology is calculated by comparing one to another when aligned to corresponding portions of the reference sequence.

In general, the stability of a hybrid is a function of the ion concentration and temperature. Typically, a hybridization reaction is performed under conditions of lower stringency, followed by washes of varying, but higher, stringency. Moderately stringent hybridization refers to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions are conditions equivalent to hybridization in 50% formamide, 5×Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C. Low stringency hybridization refers to conditions equivalent to hybridization in 10% formamide, 5×Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M EDTA. Other suitable moderate stringency and high stringency hybridization buffers and conditions are well known to those of skill in the art and are described, for example, in Sambrook et al., Molecular Cloning: A Laboratory Manual, 2nd ed., Cold Spring Harbor Press, Plainview, N.Y. (1989); and Ausubel et al., Short Protocols in Molecular Biology, 4th ed., John Wiley & Sons (1999).

Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See M. Kanehisa Nucleic Acids Res. 12:203 (1984).

The terms "homologous", "substantially homologous", and "substantial homology" as used herein denote a sequence of amino acids having at least 50%, 60%, 70%, 80% or 90% identity wherein one sequence is compared to a reference sequence of amino acids. The percentage of sequence identity or homology is calculated by comparing one to another when aligned to corresponding portions of the reference sequence.

"Multiplexing" or "multiplex assay" herein refers to an assay or other analytical method in which the presence of multiple target molecules can be assayed simultaneously, e.g., by using more than one capture probe conjugate, each of which has at least one different detection characteristic, e.g., fluorescence characteristic (for example excitation wavelength, emission wavelength, emission intensity, FWHM (full width at half maximum peak height), or fluorescence lifetime).

It is understood that aspects and embodiments of the disclosure herein include "consisting" and/or "consisting essentially of" aspects and embodiments.

Other objects, advantages and features of the present disclosure will become apparent from the following specification taken in conjunction with the accompanying drawings.

B. LUMINOPHORE

A luminophore is an atom or atomic grouping in a chemical compound that manifests luminescence. There exist organic and inorganic luminophores. Luminophores can be divided into two subcategories: fluorophores and phosphors. The difference between luminophores belonging to these two subcategories is derived from the nature of the excited state responsible for the emission of photons. Some luminophores, however, cannot be classified as being exclusively fluorophores or phosphors and exist in the gray area in between. Such cases include transition metal complexes (such as ruthenium tris-2,2'-bipyridine) whose luminescence comes from an excited (nominally triplet) metal-to-ligand charge transfer (MLCT) state, but which is not a true triplet-state in the strict sense of the definition. Most luminophores comprise conjugated pi systems or transition metal complexes. There exist purely inorganic luminophores, such as zinc sulfide doped with rare earth metal ions, rare earth metal oxysulfides doped with other rare earth metal ions, yttrium oxide doped with rare earth metal ions, zinc orthosilicate doped with manganese ions, etc.

A chromophore is a region in a molecule where the energy difference between two different molecular orbitals falls within the range of the visible spectrum. Visible light that hits the chromophore can thus be absorbed by exciting an electron from its ground state into an excited state. In biological molecules that serve to capture or detect light energy, the chromophore is the moiety that causes a conformational change of the molecule when hit by light. Chromophores almost always arise in one of two forms: conjugated pi systems and metal complexes. In the former, the energy levels that the electrons jump between are extended pi orbitals created by a series of alternating single and double bonds, often in aromatic systems. Common examples include retinal (used in the eye to detect light), various food colorings, fabric dyes (azo compounds), lycopene, β-carotene, and anthocyanins. The metal complex chromophores arise from the splitting of d-orbitals by binding of a transition metal to ligands. Examples of such chromophores can be seen in chlorophyll (used by plants for photosynthesis), hemoglobin, hemocyanin, and colorful minerals such as malachite and amethyst.

A fluorophore, in analogy to a chromophore, is a component of a molecule which causes a molecule to be fluorescent. It is a functional group in a molecule which will absorb energy of a specific wavelength and re-emit energy at a different (but equally specific) wavelength. The amount and wavelength of the emitted energy depend on both the fluorophore and the chemical environment of the fluorophore. This technology has particular importance in the field of biochemistry and protein studies, e.g., in immunofluorescence and immunohistochemistry. Fluorescein isothiocyanate (FITC), a reactive derivative of fluorescein, has been one of the most common fluorophores chemically attached to other, non-fluorescent molecules to create new fluorescent molecules for a variety of applications. Other common fluorophores include derivatives of rhodamine (TRITC), coumarin, cyanine, the CF Dyes, the FluoProbes, the DyLight Fluors, the Oyester (dyes), the Atto dyes, the HiLyte Fluors, and the Alexa Fluors.

These fluorophores can be quantum dots, protein (e.g., green fluorescent protein (GFP)) or small molecules. Common small molecule dye families include: xanthene derivatives (fluorescein, rhodamine, Oregon green, eosin, texas red, etc.), cyanine derivatives (cyanine, indocarbocyanine, oxacarbocyanine, thiacarbocyanine, merocyanine, etc.), naphthalene derivatives (dansyl and prodan derivatives), coumarin derivatives, oxadiazole derivatives (pyridyloxazole, nitrobenzoxadiazole, benzoxadiazole, etc.), pyrene derivatives (cascade blue, etc.), BODIPY (Invitrogen), oxazine derivatives (Nile red, Nile blue, cresyl violet, oxazine 170, etc.), acridine derivatives (proflavin, acridine orange, acridine yellow, etc.), arylmethine derivatives (auramine, crystal violet, malachite green, etc.), CF dye (Biotium), Alexa Fluor (Invitrogen), Atto and Tracy (Sigma), Tetrapyrrole derivatives (porphin, phtalocyanine, bilirubin, etc.), and others (cascade yellow, azure B, acridine orange, DAPI, Hoechst 33258, lucifer yellow, piroxicam, quinine and anthraqinone, squarylium, oligophenylenes, etc.).

In some embodiments, phosphors (or phosphorescent moieties) comprise transition metal compounds or rare earth compounds of various types. A material can emit light either through incandescence, where all atoms radiate, or by luminescence, where only a small fraction of atoms (called emission centers or luminescence centers) emit light. In inorganic phosphors, these inhomogeneities in the crystal structure are created usually by addition of a trace amount of dopants, impurities called activators. In some cases dislocations or other crystal defects can play the role of the impurity. The wavelength emitted by the emission center is dependent on the atom itself, and on the surrounding crystal structure.

The scintillation process in inorganic materials is due to the electronic band structure found in the crystals. An incoming particle can excite an electron from the valence band to either the conduction band or the exciton band (located just below the conduction band and separated from the valence band by an energy gap). This leaves an associated hole behind, in the valence band. Impurities create electronic levels in the forbidden gap. The excitons are loosely bound electron-hole pairs which wander through the crystal lattice until they are captured as a whole by impurity centers. The latter then rapidly de-excite by emitting scintillation light (fast component). In case of inorganic scintillators, the activator impurities are typically chosen so that the emitted light is in the visible range or near-UV where photomultipliers are effective. The holes associated with electrons in the conduction band are independent from the latter. Those holes and electrons are captured successively by impurity centers exciting certain metastable states not accessible to the excitons. The delayed de-excitation of those metastable impurity states, slowed down by reliance on the low-probability forbidden mechanism, again results in light emission (slow component).

C. MICROARRAY

In a high-throughput manner, microarray technologies enable the evaluation of up to tens of thousands of molecular interactions simultaneously. Microarrays have made significant impact on biology, medicine, drug discovery. DNA microarray-based assays have been widely used, including the applications for gene expression analysis, genotyping for mutations, single nucleotide polymorphisms (SNPs), and short tandem repeats (STRs). And polypeptide and chemical microarrays have emerged as two important tools in the field of proteomics. Chemical microarray, a form of combinatorial libraries, can also be used for lead identification, as well as optimization of these leads. In this era of bioterrorism, the development of a microarray capable of detecting a multitude of biological or chemical agents in the environment will be of great interest to the law enforcement agencies.

According to some embodiments of the present disclosure, assay methods for analysis of molecular interactions are provided. According to some embodiments of the present disclosure, assay methods for multiplexed analysis of target polynucleotides are provided. The inventive technology improves specificity and sensitivity of microarray-based assays while reducing the cost of performing genetic assays.

The target molecules include polynucleotides, polypeptides, antibodies, small molecule compounds, peptides, and carbohydrates.

As those of ordinary skill in the art will recognize, the present disclosure has an enormous number of applications, especially in assays and techniques for pharmaceutical development and diagnostics. The assays may be designed, for example, to detect polynucleotide molecules associated with any of a number of infectious or pathogenic agents including fungi, bacteria, mycoplasma, *rickettsia*, *chlamydia*, viruses, and protozoa, or to detect polynucleotide fragments associated with sexually transmitted disease, pulmonary disorders, gastrointestinal disorders, cardiovascular disorders, etc.

A microarray is a multiplex technology widely used in molecular biology and medicine. Microarrays can be fabricated using a variety of technologies, including printing with fine-pointed pins, photolithography using pre-made masks, photolithography using dynamic micromirror devices, ink-jet printing, microcontact printing, or electrochemistry on microelectrode arrays. In standard microarrays, the probe molecules are attached via surface engineering to a solid surface of supporting materials, which include glass, silicon, plastic, hydrogels, agaroses, nitrocellulose and nylon.

The microarray results for the detection of fluorescence-labeled target molecules can be viewed with a suitable method, e.g., by a CCD in bright field (left panel), under a fluorescence microscopy (middle panel), and by a commercial fluorescence microarray scanner with pseudo-color processing (right panel).

For DNA microarray, it comprises an arrayed series of microscopic spots of DNA oligonucleotides, known as probes. This can be a short section of a gene or other DNA element that are used to hybridize a complementary polynucleotide sample (called target) under stringent conditions. Targets in solution are usually detected and quantified by detection of fluorophore-, silver-, or chemiluminescence-labeled targets hybridized on microarray. Since an array can contain several to tens of thousands of probes, a microarray experiment can accomplish many genetic tests in parallel.

The systems described herein may comprise two or more probes that detect the same target polynucleotide. For example, in some embodiments where the system is a microarray, the probes may be present in multiple (such as any of 2, 3, 4, 5, 6, 7, or more) copies on the microarray. In some embodiments, the system comprises different probes that detect the same target polynucleotide. For example, these probes may bind to different (overlapping or non-overlapping) regions of the target polynucleotide.

Any probes that are capable of determining the levels of target polynucleotide can be used. In some embodiments, the probe may be an oligonucleotide. It is understood that, for detection of target polynucleotides, certain sequence variations are acceptable. Thus, the sequence of the oligonucleotides (or their complementary sequences) may be slightly different from those of the target polynucleotides described herein. Such sequence variations are understood by those of ordinary skill in the art to be variations in the sequence that do not significantly affect the ability of the oligonucleotide to determine target polynucleotide levels. For example, homologs and variants of these oligonucleotide molecules possess a relatively high degree of sequence identity when aligned using standard methods. Oligonucleotide sequences encompassed by the present disclosure have at least 40%, including for example at least about any of 50%, 60%, 70%, 80%, 90%, 95%, 99%, or 100% sequence identity to the sequence of the target polynucleotides described herein. In some embodiments, the oligonucleotide comprises a portion for detecting the target polynucleotides and another portion. Such other portion may be used, for example, for attaching the oligonucleotides to a substrate. In some embodiments, the other portion comprises a non-specific sequence (such as poly-T or poly-dT) for increasing the distance between the complementary sequence portion and the surface of the substrate.

The oligonucleotides for the systems described herein include, for example, DNA, RNA, PNA, ZNA, LNA, combinations thereof, and/or modified forms thereof. They may also include a modified oligonucleotide backbone. In some embodiments, the oligonucleotide comprises at least about any of 5, 6, 7, 8, 9, 10, 12, 13, 14, 15, 16, 17, 18, 19, 20, or more continuous oligonucleotides complementary or identical to all or part of target polynucleotides described herein. A single oligonucleotide may comprise two or more such complementary sequences. In some embodiments, there may be a reactive group (such as an amine) attached to the 5' or 3' end of the oligonucleotide for attaching the oligonucleotide to a substrate.

In some embodiments, the probes are oligonucleotides. Oligonucleotides forming the array may be attached to the substrate by any number of ways including, but not limiting to, (i) in situ synthesis (e.g., high-density oligonucleotide arrays) using photolithographic techniques; (ii) spotting/printing at medium to low density on glass, silicon, nylon or nitrocellulose; (iii) masking; and (iv) dot-blotting on a nylon or nitrocellulose hybridization membrane. Oligonucleotides may also be non-covalently immobilized on the substrate by binding to anchors in a fluid phase such as in microtiter wells, microchannels or capillaries.

Several techniques are well-known in the art for attaching polynucleotides to a solid substrate such as a glass slide. One method is to incorporate modified bases or analogs that contain a moiety that is capable of attachment to a solid substrate, such as an amine group, a derivative of an amine group or another group with a positive charge, into the amplified polynucleotides. The amplified product is then contacted with a solid substrate, such as a glass slide, which may be coated with an aldehyde or another reactive group which can form a covalent link with the reactive group that is on the amplified product and become covalently attached to the glass slide. Microarrays comprising the amplified products can be fabricated using a Biodot (BioDot, Inc. Irvine, Calif.) spotting apparatus and aldehyde-coated glass slides (CEL Associates, Houston, Tex.). Amplification products can be spotted onto the aldehyde-coated slides, and processed according to published procedures (Schena et al., Proc. Natl. Acad. Sci. U.S.A. (1995), 93:10614-10619). Arrays can also be printed by robotics onto glass, nylon (Ramsay, G., Nature Biotechnol. (1998), 16:40-44), polypropylene (Matson, et al., Anal Biochem. (1995), 224(1): 110-6), and silicone slides (Marshall and Hodgson, Nature Biotechnol. (1998), 16:27-31). Other approaches to array assembly include fine micropipetting within electric fields (Marshall, and Hodgson, Nature Biotechnol. (1998), 16:27-31), and spotting the polynucleotides directly onto positively coated plates. Methods such as those using amino propyl silicon surface chemistry are also known in the art, as disclosed at cmgm.stanford.edu/pbrown/.

The assays of the present disclosure may be implemented in a multiplex format. Multiplex methods are provided employing 2, 3, 4, 5, 10, 15, 20, 25, 50, 100, 200, 500, 1000 or more different capture probes which can be used simultaneously to assay for amplification products from corresponding different target polynucleotides. In some embodiments, multiplex methods can also be used to assay for polynucleotide target sequences which have not undergone an amplification procedure. Methods amenable to multiplexing, such as those taught herein, allow acquisition of greater amounts of information from smaller specimens. The need for smaller specimens increases the ability of an investigator to obtain samples from a larger number of individuals in a population to validate a new assay or simply to acquire data, as less invasive techniques are needed.

Where different substrates are included in a multiplex assay as part of the capture probe conjugates, the different substrates can be encoded so that they can be distinguished. Any encoding scheme can be used; conveniently, the encoding scheme can employ one or more different fluorophores, which can be fluorescent semiconductor nanocrystals. High density spectral coding schemes can be used.

One or more different populations of spectrally encoded capture probe conjugates can be created, each population comprising one or more different capture probes attached to a substrate comprising a known or determinable spectral code comprising one or more semiconductor nanocrystals or fluorescent nanoparticle. Different populations of the conjugates, and thus different assays, can be blended together, and the assay can be performed in the presence of the blended populations. The individual conjugates are scanned for their spectral properties, which allows the spectral code to be decoded and thus identifies the substrate, and therefore the capture probe(s) to which it is attached. Because of the large number of different semiconductor nanocrystals and fluorescent nanoparticles and combinations thereof which can be distinguished, large numbers of different capture probes and amplification products can be simultaneously interrogated.

D. PARTICLES

The present disclosure provides particles, microparticles or beads, preferably magnetic beads, to be used for the microarray-based assay. Particles or beads can be prepared from a variety of different polymers, including but not limited to polystyrene, cross-linked polystyrene, polyacrylic acid, polylactic acid, polyglycolic acid, poly(lactide coglycolide), polyanhydrides, poly(methyl methacrylate), poly (ethylene-co-vinyl acetate), polysiloxanes, polymeric silica, latexes, dextran polymers and epoxies. The materials have a variety of different properties with regard to swelling and porosity, which are well understood in the art. Preferably, the beads are in the size range of approximately 10 nanometers to 1 millimeter, preferably 100 nanometers to 10 micrometers, and can be manipulated using normal solution techniques when suspended in a solution. The terms "particle," "bead," "sphere," "microparticle," "microbead" and "microsphere" are used interchangeably herein.

The suitable chemical compositions for the magnetic particles may be ferromagnetic materials and include rare earth containing materials such as, e.g., iron-cobalt, iron-platinum, samarium-cobalt, neodynium-iron-boride, and the like. Other magnetic materials, e.g., superparamagnetic materials such as iron oxides ($Fe_3O_4$) may be used as well. Among the preferred magnetic materials are included iron-cobalt as such material is generally easier to magnetize, has a stronger magnetization (about 1.7 Tesla) and is less susceptible to corrosion.

Because of the use of particles, expensive readout devices for results may not be necessary. Particles on the microarray spots can be viewed directly with naked eyes if the sizes in diameters of these spots are larger than 0.03 millimeters. In another way, assay results with any spot sizes, from 0.01 millimeters to 5 millimeters in diameter, can be photographed with an ordinary camera or viewed under an appropriate magnification microscope.

E. TARGET POLYNUCLEOTIDE

The target polynucleotide can be single-stranded, double-stranded, or higher order, and can be linear or circular. Exemplary single-stranded target polynucleotides include mRNA, rRNA, tRNA, hnRNA, microRNA, ssRNA or ssDNA viral genomes and viroids, although these polynucleotides may contain internally complementary sequences and significant secondary structure. Exemplary double-stranded target polynucleotides include genomic DNA, mitochondrial DNA, chloroplast DNA, dsRNA or dsDNA viral genomes, plasmids, phages, shRNA (a small hairpin RNA or short hairpin RNA), and siRNA (small/short interfering RNA). The target polynucleotide can be prepared recombinantly, synthetically or purified from a biological source. The target polynucleotide may be purified to remove or diminish one or more undesired components of the sample or to concentrate the target polynucleotide prior to amplification. Conversely, where the target polynucleotide is too concentrated for a particular assay, the target polynucleotide may first be diluted.

Following sample collection and optional nucleic acid extraction and purification, the nucleic acid portion of the sample comprising the target polynucleotide can be subjected to one or more preparative treatments. These preparative treatments can include in vitro transcription (IVT), labeling, fragmentation, amplification and other reactions. mRNA can first be treated with reverse transcriptase and a primer, which can be the first primer comprising the target non-complementary region, to create cDNA prior to detection and/or further amplification; this can be done in vitro with extracted or purified mRNA or in situ, e.g., in cells or tissues affixed to a slide. Nucleic acid amplification increases the copy number of sequences of interest and can be used to incorporate a label into an amplification product produced from the target polynucleotide using a labeled primer or labeled nucleotide. A variety of amplification methods are suitable for use, including the polymerase chain reaction method (PCR), transcription mediated amplification (TMA), the ligase chain reaction (LCR), self sustained sequence replication (3SR), nucleic acid sequence-based amplification (NASBA), rolling circle amplification (RCA), loop-mediated isothermal amplification (LAMP), the use of Q Beta replicase, reverse transcription, nick translation, and the like, particularly where a labeled amplification product can be produced and utilized in the methods taught herein.

Any nucleotides may be detected by the present devices and methods. Examples of such nucleotides include AMP, GMP, CMP, UMP, ADP, GDP, CDP, UDP, ATP, GTP, CTP, UTP, dAMP, dGMP, dCMP, dTMP, dADP, dGDP, dCDP, dTDP, dATP, dGTP, dCTP and dTTP.

In some embodiments, the target polynucleotide does not have a label directly incorporated in the sequence. When the target polynucleotide is made with a directly incorporated label or so that a label can be directly bound to the target polynucleotide, this label is one which does not interfere with detection of the capture probe conjugate substrate and/or the report moiety label.

Where the target polynucleotide is single-stranded, the first cycle of amplification forms a primer extension product complementary to the target polynucleotide. If the target polynucleotide is single-stranded RNA, a reverse transcriptase is used in the first amplification to reverse transcribe the RNA to DNA, and additional amplification cycles can be performed to copy the primer extension products. The primers for a PCR must, of course, be designed to hybridize to regions in their corresponding template that will produce an amplifiable segment; thus, each primer must hybridize so that its 3' nucleotide is base-paired with a nucleotide in its corresponding template strand that is located 3' from the 3' nucleotide of the primer used to prime the synthesis of the complementary template strand.

The target polynucleotide may be amplified by contacting one or more strands of the target polynucleotide with a primer and a polymerase having suitable activity to extend the primer and copy the target polynucleotide to produce a full-length complementary polynucleotide or a smaller portion thereof. Any enzyme having a polymerase activity which can copy the target polynucleotide can be used, including DNA polymerases, RNA polymerases, reverse transcriptases, enzymes having more than one type of polymerase activity. The polymerase can be thermolabile or thermostable. Mixtures of enzymes can also be used. Exemplary enzymes include: DNA polymerases such as DNA Polymerase I ("Pol I"), the Klenow fragment of Pol I, T4, T7, Sequenase™ T7, Sequenase™ Version 2.0 T7, Tub, Taq, Tth, Pfx, Pfu, Tsp, Tfl, Tli and *Pyrococcus* sp GB-D DNA polymerases; RNA polymerases such as *E. coli*, SP6, T3 and T7 RNA polymerases; and reverse transcriptases such as AMV, M-MuLV, MMLV, RNAse H minus MMLV (SuperScript™), SuperScript™ II, ThermoScript™, HTV-1, and RAV2 reverse transcriptases. All of these enzymes are commercially available. Exemplary polymerases with multiple specificities include RAV2 and Tli (exo-) polymerases. Exemplary thermostable polymerases include Tub, Taq, Tth, Pfx, Pfu, Tsp, Tfl, Tli and *Pyrococcus* sp. GB-D DNA polymerases.

Suitable reaction conditions are chosen to permit amplification of the target polynucleotide, including pH, buffer, ionic strength, presence and concentration of one or more salts, presence and concentration of reactants and cofactors such as nucleotides and magnesium and/or other metal ions, optional co-solvents, temperature, thermal cycling profile for amplification schemes comprising a polymerase chain reaction, and may depend in part on the polymerase being used as well as the nature of the sample. Co-solvents include formamide (typically at from about 2 to about 10%), glycerol (typically at from about 5 to about 10%), and DMSO (typically at from about 0.9 to about 10%). Techniques may be used in the amplification scheme in order to minimize the production of false positives or artifacts produced during amplification. These include "touchdown" PCR, hot-start techniques, use of nested primers, or designing PCR primers so that they form stem-loop structures in the event of primer-dimer formation and thus are not amplified. Techniques to accelerate PCR can be used, for example centrifugal PCR, which allows for greater convection within the sample, and comprising infrared heating steps for rapid heating and cooling of the sample. One or more cycles of amplification can be performed. An excess of one primer can be used to produce an excess of one primer extension product during PCR; preferably, the primer extension product produced in excess is the amplification product to be detected. A plurality of different primers may be used to amplify different regions of a particular polynucleotide within the sample. Where the amplification reaction comprises multiple cycles of amplification with a polymerase, as in PCR, it is desirable to dissociate the primer extension product(s) formed in a given cycle from their template(s). The reaction conditions are therefore altered between cycles to favor such dissociation; typically this is done by elevating the temperature of the reaction mixture, but other reaction conditions can be altered to favor dissociation, for example lowering the salt concentration and/or raising the pH of the solution in which the double-stranded polynucleotide is dissolved. Although it is preferable to perform the dissociation in the amplification reaction mixture, the polynucleotides may be first isolated using any effective technique and transferred to a different solution for dissociation, then reintroduced into an amplification reaction mixture for additional amplification cycles.

In some aspects, the assay disclosed herein can be multiplexed, e.g., multiple distinct assays can be run simultaneously, by using different pairs of primers directed at different targets, which can be unrelated targets, or different alleles or subgroups of alleles from, or chromosomal rearrangements at, the same locus. This allows the quantitation of the presence of multiple target polynucleotides in a sample (e.g., specific genes in a cDNA library). All that is required is an ability to uniquely identify the different second polynucleotide extension products in such an assay, through either a unique capture sequence or a unique label.

Amplified target polynucleotides may be subjected to post-amplification treatments. For example, in some cases, it may be desirable to fragment the amplification products prior to hybridization with a polynucleotide array, in order to provide segments which are more readily accessible and which avoid looping and/or hybridization to multiple capture probes. Fragmentation of the polynucleotides can be carried out by any method producing fragments of a size useful in the assay being performed; suitable physical, chemical and enzymatic methods are known in the art.

Amplified target polynucleotides may also be coupled to the particles, either directly or through modifications to the polynucleotides and/or the particles. In some embodiments, the target polynucleotides are modified, such as biotinylation. In some other embodiments, the particles are modified with a functional group, such as streptavidin, neutravidin, avidin, etc. The target polynucleotides may be coupled to the particles through such modifications and functional groups. For double stranded polynucleotides, following the coupling of the target polynucleotides to the particles, single-stranded target polynucleotides can be prepared by denaturation methods by a chemical reaction, enzyme or heating, or a combination thereof, while coupled to the particles. In some embodiments, the chemical reaction uses urea, formamide, methanol, ethanol, an enzyme, or NaOH. In some embodiments, enzymatic methods include exonuclease and Uracil-N-glycosylase. In some other embodiments, the double-stranded target polynucleotide is heat denatured at an appropriate temperature from about 30° C. to about 95° C.

The method of the present disclosure is suitable for use in a homogeneous multiplex analysis of multiple target polynucleotides in a sample. Multiple target polynucleotides can be generated by amplification of a sample by multiple amplification oligonucleotide primers or sets of primers, each primer or set of primers specific for amplifying a particular polynucleotide target sequence. For example, a sample can be analyzed for the presence of multiple viral polynucleotide target sequences by amplification with primers specific for amplification of each of multiple viral target sequences, including, e.g., human immunodeficiency virus (HIV), hepatitis B virus (HBV), hepatitis C virus (HCV), hepatitis A virus (HAV), parvovirus B19, West Nile Virus, hantavirus, severe acute respiratory syndrome-associated coronavirus (SARS), etc.

The portion of the sample comprising or suspected of comprising the target polynucleotide can be any source of biological material which comprises polynucleotides that can be obtained from a living organism directly or indirectly, including cells, tissue or fluid, and the deposits left by that organism, including viruses, mycoplasma, and fossils. The sample can also comprise a target polynucleotide prepared through synthetic means, in whole or in part. Typically, the sample is obtained as or dispersed in a predominantly aqueous medium. Non-limiting examples of the sample include blood, plasma, urine, semen, milk, sputum, mucus, a buccal swab, a vaginal swab, a rectal swab, an aspirate, a needle biopsy, a section of tissue obtained for example by surgery or autopsy, plasma, serum, spinal fluid, lymph fluid, the external secretions of the skin, respiratory, intestinal, and genitourinary tracts, tears, saliva, tumors, organs, samples of in vitro cell culture constituents (including but not limited to conditioned medium resulting from the growth of cells in cell culture medium, putatively virally infected cells, recombinant cells, and cell components), and a recombinant source, e.g., a library, comprising polynucleotide sequences.

The sample can be a positive control sample which is known to contain the target polynucleotide or a surrogate thereof. A negative control sample can also be used which, although not expected to contain the target polynucleotide, is suspected of containing it, and is tested in order to confirm the lack of contamination by the target polynucleotide of the reagents used in a given assay, as well as to determine whether a given set of assay conditions produces false positives (a positive signal even in the absence of target polynucleotide in the sample).

The sample can be diluted, dissolved, suspended, extracted or otherwise treated to solubilize and/or purify any target polynucleotide present or to render it accessible to reagents which are used in an amplification scheme or to detection reagents. Where the sample contains cells, the cells can be lysed or permeabilized to release the polynucleotides within the cells. Permeabilization buffers can be used to lyse cells which allow further steps to be performed directly after lysis, for example a polymerase chain reaction.

F. GENETIC INFORMATION

Any kind of genetic information can be the subject of the presently claimed method of microarray based analysis. For example, the genetic information may be a mutation selected from the group consisting of a substitution, an insertion, a deletion and an indel. In one embodiment, the genetic information is a single nucleotide polymorphism (SNP). In one embodiment, the genetic information is a gene. In one embodiment, the genetic information is a genetic product including a polypeptide, an antibody, a small molecule compound, a peptide and a carbohydrate. In another embodiment, the genetic information is associated with a disease caused by an infectious or pathogenic agent selected from the group consisting of a fungus, a bacterium, a mycoplasma, a rickettsia, a chlamydia, a virus and a protozoa. In yet another embodiment, the genetic information is associated with a sexually transmitted disease, cancer, cerebrovascular disease, heart disease, respiratory disease, coronary heart disease, diabetes, hypertension, Alzheimer's disease, neurodegenerative disease, chronic obstructive pulmonary disease, autoimmune disease, cystic fibrosis, spinal muscular atrophy, beta thalassemia, phenylalanine hydroxylase deficiency, Duchenne muscular dystrophy, or hereditary hearing loss. In still another embodiment, the genetic information is associated with hereditary hearing loss.

The allele of the target gene may be caused by single base substitution, insertion, or deletion, or by multiple-base substitution, insertion or deletion, or indel. Furthermore, modifications to nucleotidic units include rearranging, appending, substituting for or otherwise altering functional groups on the purine or pyrimidine base which form hydrogen bonds to a respective complementary pyrimidine or purine. The resultant modified nucleotidic unit optionally may form a base pair with other such modified nucleotidic units but not with A, T, C, G or U. Basic sites may be incorporated which do not prevent the function of the polynucleotide. Some or all of the residues in the polynucleotide can optionally be modified in one or more ways.

Standard A-T and G-C base pairs form under conditions which allow the formation of hydrogen bonds between the N3-H and C4-oxy of thymidine and the N1 and C6-NH2, respectively, of adenosine and between the C2-oxy, N3 and C4-NH2, of cytidine and the C2-NH2, N'—H and C6-oxy, respectively, of guanosine. Thus, for example, guanosine (2-amino-6-oxy-9-O-D-ribofuran-osyl-purine) may be modified to form isoguanosine (2-oxy-6-amino-9-β-D-ribofuranosyl-purine). Such modification results in a nucleoside base which will no longer effectively form a standard base pair with cytosine. However, modification of cytosine (1-β-D-ribofuranosyl-2-oxy-4-amino-pyrimidine) to form isocytosine (1-β-D-ribofuranosyl-2-amino-4-oxy-pyrimidine) results in a modified nucleotide which will not effectively base pair with guanosine but will form a base pair with isoguanosine (U.S. Pat. No. 5,681,702). Isocytosine is available from Sigma Chemical Co. (St. Louis, Mo.); isocytidine may be prepared by the method described by Switzer et al. (1993) Biochemistry 32:10489-10496 and references cited therein; 2'-deoxy-5-methyl-isocytidine may be prepared by the method of Tor et al. (1993) J. Am. Chem. Soc. 115: 4461-4467 and references cited therein; and isoguanine nucleotides may be prepared using the method described by Switzer et al. (1993), supra, and Mantsch et al. (1993) Biochem. 14:5593-5601, or by the method described in U.S. Pat. No. 5,780,610. Other normatural base pairs may be synthesized by the method described in Piccirilli et al. (1990) Nature 343:33-37 for the synthesis of 2,6-diaminopyrimidine and its complement (1-methylpyrazolo-[4,3]pyrimidine-5,7-(4H,6H)-dione). Other such modified nucleotidic units which form unique base pairs are known, such as those described in Leach et al. (1992) J. Am. Chem. Soc. 114:3675-3683 and Switzer et al., supra.

A polymorphic region as defined herein is a portion of a genetic locus that is characterized by at least one polymorphic site. A genetic locus is a location on a chromosome which is associated with a gene, a physical feature, or a phenotypic trait. A polymorphic site is a position within a genetic locus at which at least two alternative sequences have been observed in a population. A polymorphic region as defined herein is said to "correspond to" a polymorphic site, that is, the region may be adjacent to the polymorphic site on the 5' side of the site or on the 3' side of the site, or alternatively may contain the polymorphic site. A polymorphic region includes both the sense and antisense strands of the polynucleotide comprising the polymorphic site, and may have a length of from about 100 to about 5000 base pairs. For example, a polymorphic region may be all or a portion of a regulatory region such as a promoter, 5' UTR, 3' UTR, an intron, an exon, or the like. A polymorphic or allelic variant is a genomic DNA, cDNA, mRNA or polypeptide having a nucleotide or amino acid sequence that comprises a polymorphism. A polymorphism is a sequence variation observed at a polymorphic site, including nucleotide substitutions (single nucleotide polymorphisms or SNPs), insertions, deletions, indels and microsatellites. Polymorphisms may or may not result in detectable differences in gene expression, protein structure, or protein function. Preferably, a polymorphic region of the present disclosure has a length of about 1000 base pairs. More preferably, a polymorphic region of the present disclosure has a length of about 500 base pairs. Most preferably, a polymorphic region of the present disclosure has a length of about 200 base pairs.

A haplotype as defined herein is a representation of the combination of polymorphic variants in a defined region within a genetic locus on one of the chromosomes in a chromosome pair. A genotype as used herein is a representation of the polymorphic variants present at a polymorphic site.

Those of ordinary skill will recognize that oligonucleotides complementary to the polymorphic regions described herein must be capable of hybridizing to the polymorphic regions under conditions of stringency such as those employed in primer extension-based sequence determination methods, restriction site analysis, nucleic acid amplification methods, ligase-based sequencing methods, mismatch-based sequence determination methods, microarray-based sequence determination methods, and the like.

Congenital hearing loss affects one in 1,000 live births and approximately 50% of these cases are hereditary. Among Chinese disabled persons, hearing loss population is the second largest. SNPs/mutations in GJB2, SLC26A4 and 12S rRNA are the prevalent causes of inherited hearing loss. In one aspect, the present disclosure meets the need of SNP/mutation detection from various deafness patients or even healthy persons, which also serves as an example to support the applicability of a method disclosed herein.

G. OLIGONUCLEOTIDE PRIMERS FOR AMPLIFICATION OF TARGET POLYNUCLEOTIDES

In certain aspects, the present disclosure is also embodied in oligonucleotide primer pairs suitable for use in the polymerase chain reaction (PCR) or in other nucleic acid amplification methods. Those of ordinary skill will be able to design suitable oligonucleotide primer pairs using knowledge readily available in the art, in combination with the teachings herein. Specific oligonucleotide primer pairs of this embodiment include the oligonucleotide primer pairs set forth in Table 2, which are suitable for amplifying the polymorphic regions corresponding to polymorphic sites in GJB2, SLC26A4 and 12S rRNA. Those of ordinary skill will recognize that other oligonucleotide primer pairs suitable for amplifying the polymorphic regions in GJB2, SLC26A4 and 12S rRNA can be designed without undue experimentation.

In some variations a SNP/mutation corresponds to at least two allele-specific primers. One allele-specific primer comprises a sequence identical or complementary to a region of the wild-type allele of a target fragment containing the SNP/mutation locus. Each of the other allele-specific primers comprises a sequence identical or complementary to a region of the mutant allele of a target fragment containing the SNP/mutation locus. The allele-specific primers may terminate at their 3' ends at the SNP/mutation locus. To increase the capability of differentiation between the wild-type and mutant alleles of target genes, an artificial mismatch in the allele-specific primers may be introduced. The artificial mismatch can be a natural base or a nucleotide analog. Each of the PCR primer pairs of the present disclosure may be used in any PCR method. For example, a PCR primer pair of the present disclosure may be used in the methods disclosed in U.S. Pat. Nos. 4,683,195; 4,683,202; 4,965,188; 5,656,493; 5,998,143; 6,140,054; WO 01/27327; WO 01/27329; and the like. The PCR primer pairs of the present disclosure may also be used in any of the commercially available machines that perform PCR, such as any of the GeneAmp® Systems available from Applied Biosystems.

The present primers can comprise any suitable types of nucleic acids, e.g., DNA, RNA, PNA or a derivative thereof. Preferably, the primers comprise a nucleotide sequence, or a complementary strand thereof, that is set forth in Table 2. Also preferably, the primers are labeled, e.g., a chemical, an enzymatic, an immunogenic, a radioactive, a fluorescent, a luminescent and a FRET label.

The oligonucleotide primers can be produced by any suitable method. For example, the primers can be chemically synthesized (Sec generally, Ausubcl (Ed.) Current Protocols in Molecular Biology, 2.11. Synthesis and purification of oligonucleotides, John Wiley & Sons, Inc. (2000)), isolated from a natural source, produced by recombinant methods or a combination thereof. Synthetic oligonucleotides can also be prepared by using the triester method of Matteucci et al., J. Am. Chem. Soc., 3:3185-3191 (1981). Alternatively, automated synthesis may be preferred, for example, on an Applied Biosynthesis DNA synthesizer using cyanoethyl phosphoramidite chemistry. Preferably, the primers are chemically synthesized.

Suitable bases for preparing the oligonucleotide primers of the present disclosure may be selected from naturally occurring nucleotide bases such as adenine, cytosine, guanine, uracil, and thymine. It may also be selected from nonnaturally occurring or "synthetic" nucleotide bases such as 8-oxo-guanine, 6-mercaptoguanine, 4-acetylcytidine, 5-(carboxyhydroxyethyl) uridine, 2'-O-methylcytidine, 5-carboxymethylamino-methyl-2-thioridine, 5-carboxymethylaminomethyl uridine, dihydrouridine, 2'-O-methylpseudouridine, beta-D-galactosylqueosine, 2'-Omethylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, beta-D-mannosylqueosine, 5-methoxycarbonylmethyluridine, 5-methoxyuridine, 2-methylthio-N6-isopentenyladenosine, N-((9-.beta.-D-ribofuranosyl-2-methylthiopurine-6-yl)carbamoyl)threonine, N-((9-beta-D-ribofuranosylpurine-6-yl) N-methyl carbamoyl) threonine, uridine-5-oxyacetic acid methylester, uridine-5-oxyacetic acid, wybutoxosine, pseudouridine, queosine, 2-thiocytidine, 5-methyl-2-thiouridine, 2-thiouridine, 2-thiouridine, 5-methyluridine, N-((9-beta-D-ribofuranosylpurine-6-yl) carbamoyl) threonine, 2'-O-methyl-5-methyluridine, 2'-O-methyluridine, wybutosine, and 3-β-amino-3-carboxypropyl) uridine.

Likewise, chemical analogs of oligonucleotides (e.g., oligonucleotides in which the phosphodiester bonds have been modified, e.g., to the methylphosphonate, the phosphotriester, the phosphorothioate, the phosphorodithioate, or the phosphoramidate) may also be employed. Protection from degradation can be achieved by use of a "3'-end cap" strategy by which nuclease-resistant linkages are substituted for phosphodiester linkages at the 3' end of the oligonucleotide (Shaw et al., Nucleic Acids Res., 19:747 (1991)). Phosphoramidates, phosphorothioates, and methylphosphonate linkages all function adequately in this manner. More extensive modification of the phosphodiester backbone has been shown to impart stability and may allow for enhanced affinity and increased cellular permeation of oligonucleotides (Milligan et al., J. Med. Chem., 36:1923 (1993)). Many different chemical strategies have been employed to replace the entire phosphodiester backbone with novel linkages. Backbone analogues include phosphorothioate, phosphorodithioate, methylphosphonate, phosphoramidate, boranophosphate, phosphotriester, fon-nacetal, 3'-thioformacetal, 5'-thioformacetal, 5'-thioether, carbonate, 5'-N-carbamate, sulfate, sulfonate, sulfamate, sulfonamide, sulfone, sulfite, sulfoxide, sulfide, hydroxylamine, methylene (methylimino) (MMI) or methyleneoxy (methylimino) (MOMI) linkages. Phosphorothioate and methylphosphonate-modified oligonucleotides are particularly preferred due to their availability through automated oligonucleotide synthesis. The oligonucleotide may be a "peptide nucleic acid" such as described by (Milligan et al., J. Med. Chem., 36:1923 (1993)). The only requirement is that the oligonucleotide primer should possess a sequence at least a portion of which is capable of binding to a portion of a target sequence.

The target polynucleotide may be double stranded or single stranded. In some embodiments, at least a portion of the single-stranded target polynucleotide is completely or substantially complementary to at least a portion of the oligonucleotide probe immobilized on the microarray. In other embodiments, the single-stranded target polynucleotide is completely complementary to the oligonucleotide probe immobilized on the microarray.

Employing PCR, RT-PCR (for RNA molecules) or other methods, polynucleotide molecules/agents of interest can be converted to nucleic acid fragments and labeled with biotin, digoxin or the similar, which then binds with moieties on the surface of particles/beads. By coupling to the particles or beads, these nucleic acid fragments in solution are enriched. For double-stranded nucleic acid fragments, they are denatured to single-stranded ones. Beads are then coupled to specific microarray spots through target-probe hybridization, which directly or through further modifications, facilitate the detection of results with non-expensive devices or common commercial microarray scanners. Specific genes, SNPs or gene mutations, such as deletions, insertions, and indels, are thus identified. For SNPs/mutations, they are valuable for biomedical research and for developing pharmaceutical compounds or medical diagnostics. SNPs arc also evolutionarily stable—not changing much from generation to generation—making them convenient to follow in population studies.

Any method may be used to assay the polynucleotide, that is, to determine the polymorphic sites, in this step of the present disclosure. For example, any of the primer extension-based methods, ligase-based sequence determination methods, mismatch-based sequence determination methods, or microarray-based sequence determination methods described above may be used, in accordance with the present disclosure. Alternatively, such methods as restriction fragment length polymorphism (RFLP) detection, single strand conformation polymorphism detection (SSCP), denaturing gradient gel electrophoresis (DGGE), denaturing high-performance liquid chromatography (DHPLC), PCR-based assays such as the Taqman® PCR System (Applied Biosystems) may be used.

Allele-specific PCR (ASPCR) is known as amplification refractory mutation system (ARMS) or PCR-sequence specific primer (PCR-SSP), etc. With high accuracy, ASPCR is suitable for analyzing known SNPs/mutations in genetic sequences, which uses DNA polymerase without the 3'-5' exonuclease activity so that if the 3' end of a specific primer does not match the template, the primer can not be elongated and the PCR reaction is blocked. Utilizing multiplex PCR, multiple loci can be amplified simultaneously, and then distinguished by DNA microarray. The PCR amplification may be conducted in one tube, or in different tubes.

By employing the universal array technology, Tag sequences are conjugated with primers, and their final products can readily hybridize with the Tag probes. Microarrays here just serve as a decode tool. The Tag sequences are artificially designed and subject to critical filtering, they have the corresponding complementary sequences, cTag sequences. Each combination of Tag and cTag corresponds to an allele of a SNP/mutation in the target gene. The Tm difference between different Tag sequences equals or is less than 5° C., and the Tag sequences have no cross-hybridization among themselves or with the group of primers, have low homology to the species of the sample genomic DNA, and no hair-pin structures. Determination of genes or genotypes is based on the hybridization signal and the position of the Tag probes on microarray hybridized with the PCR products.

For the universal tag array, one can use many more or less Tag sequences with or without replicate spots for specific applications. These Tag sequences may be designed by methods of bioinformatics. Tag probes can also be derived from a biological species different from the species of the target gene. For example, if the species of the target is from human, the Tag sequences can be derived from sequences of bacteria. In one aspect, the Tag sequence is single stranded oligonucleotide or peptide oligonucleotide.

In one aspect, the universal array disclosed herein is different from the common microarray. For common microarray, the probes on the array may be gene-specific or allele-specific oligonucleotides. Different target gene panel or SNP/mutation panel needs different format of microarray. However, the universal array in the present disclosure comprises Tag probes which are specifically designed, so they are not associated with allele-specific oligonucleotides or primers. The Tag sequences can be used as codes for different SNP/mutation of different genes or different species. One format of universal array can be used for detection of any gene or genotype. So such array is universal and the process of detection is a de-coding step.

H. KITS

A kit useful for labeling a target molecule with a luminophore for detecting the target molecule using a microarray is provided in the present disclosure. In certain aspect, the present disclosure is also embodied in a kit comprising a universal Tag array. Preferably, the kit of the present disclosure comprises set of primers for ASPCR amplification of a genetic information comprising two allele-specific primers and a common primer as set forth in Table 2. The kit of the present disclosure may also comprise a polymerizing agent, for example, a thermostable nucleic acid polymerase such as those disclosed in U.S. Pat. Nos. 4,889,818; 6,077,664, and the like. The kit of the present disclosure may also comprise chain elongating nucleotides, such as dATP, dTTP, dGTP, dCTP, and dITP, including analogs of dATP, dTTP, dGTP, dCTP and dITP, so long as such analogs are substrates for a thermostable nucleic acid polymerase and can be incorporated into a growing nucleic acid chain. In a preferred embodiment, the kit of the present disclosure comprises at least one oligonucleotide primer pair, a polymerizing agent, and chain elongating nucleotides. The kit of the present disclosure may optionally include buffers, vials, microtiter plates, and instructions for use.

In some embodiments, the kit comprises a means for labeling a subset of a plurality of target molecules with a luminophore. In some embodiments, a luminophore is attached chemically to aid in the labeling and detection of a biomolecule such as a protein, antibody, or amino acid. In some embodiments, the luminophore binds to a specific region or functional group on the target molecule and can be attached chemically or biologically. Various labeling techniques such as enzymatic labeling, protein labeling, and genetic labeling can be utilized.

In other embodiments, the kit comprises a means for labeling a subset of the plurality of functional moieties with a luminophore. In some embodiments, the kit comprises a means for labeling the labeling molecule with a luminophore. In some embodiments, the kit comprises a means for labeling the binding molecule with a luminophore. Labeling of the luminophore to the target molecule, the functional moiety, the particle, the labeling molecule, or the binding molecule can be direct labeling or indirect labeling, and can be by covalent binding or non-covalent binding. In some embodiments, the luminophore can be attached chemically or biologically. Various labeling techniques such as enzymatic labeling, protein labeling, and genetic labeling can be utilized.

In some embodiments, the kit comprises a means for introducing the luminophore into or onto the particle. For example, the luminophore can be mixed with the material of a microparticle before, during, and/or after the formation of the microparticle. The interaction between the luminophore and the particle can be direct or indirect, and can be by covalent binding or non-covalent binding. In some embodiments, the luminophore is introduced into or onto the particle by passive diffusion, active targeting (for example, via a receptor-ligand interaction), mechanical mixing, electrophoresis, or magnetic interaction between the luminophore and the particle.

In some embodiments, buccal swabs and dried blood spots from families affected by deafness are collected, and DNA is extracted and subjected to a method disclosed herein. Thus, in certain aspects, a kit disclosed herein further comprises a means for extracting DNA from a sample, for example, a biological sample. As used herein, a "biological sample" can refer to any sample obtained from a living or viral (or prion) source or other source of macromolecules and biomolecules, and includes any cell type or tissue of a subject from which nucleic acid, protein and/or other macromolecule can be obtained. The biological sample can be a sample obtained directly from a biological source or a sample that is processed. For example, isolated nucleic acids that are amplified constitute a biological sample. Biological samples include, but are not limited to, body fluids, such as blood, plasma, serum, cerebrospinal fluid, synovial fluid, urine and sweat, tissue and organ samples from animals and plants and processed samples derived therefrom. Methods for DNA extraction from biological samples are known in the art.

I. EXEMPLARY EMBODIMENTS

The following examples are offered to illustrate but not to limit the present disclosure.

Microarray-based assay integrated with paramagnetic microspheres was used for multiplexed analysis of SNPs/mutations related to hereditary hearing loss. Commercial fluorescent scanner was employed to detect the results, which were accomplished by enriching multiple PCR products with microspheres, harvesting ssDNA fragments, coupling microspheres to universal Tag array through hybridization, and decoding them with the universal Tag array.

The Tag probes on the universal array are designed according to the format: NH$_2$-TTTTTTTTTTTTTTT-TagX, where X is a natural number between 1 and 12. The Tag probes have a 5'-amino group modification, followed by poly-dT15, followed by Tag1 to Tag12 with the sequences 1 to 12 listed in Table 1, respectively. The nucleotide sequences of Tag1 to Tag12 in the Tag probes are identical to the corresponding sequences of Tag1 to Tag12 of the primers, respectively.

TABLE 1

The probes of the universal Tag array

| Name | Sequence (5'→3') | Structure |
|---|---|---|
| Tag-1 | NH$_2$-T15-GAGGAGATCGTAGCTGGTGCAT (SEQ ID NO: 1) | NH$_2$-T15-Tag1 |
| Tag-2 | NH$_2$-T15-TCGCTGCCAACCGAGAATTGCA (SEQ ID NO: 2) | NH$_2$-T15-Tag2 |
| Tag-3 | NH$_2$-T15-GAGCAAGCGCAAACGCAGTACT (SEQ ID NO: 3) | NH$_2$-T15-Tag3 |
| Tag-4 | NH$_2$-T15-GCATAGACGTGGCTCAACTGTC (SEQ ID NO: 4) | NH$_2$-T15-Tag4 |
| Tag-5 | NH$_2$-T15-CAAGGCACGTCCCAGACGCATCAA (SEQ ID NO: 5) | NH$_2$-T15-Tag5 |
| Tag-6 | NH$_2$-T15-TCGGCACGCGCGAGATCACCATC (SEQ ID NO: 6) | NH$_2$-T15-Tag6 |
| Tag-7 | NH$_2$-T15-TTTTCCCGTCCGTCATCGCTCAAG (SEQ ID NO: 7) | NH$_2$-T15-Tag7 |
| Tag-8 | NH$_2$-T15-GGTATCGCGACCGCATCCCAATCT (SEQ ID NO: 8) | NH$_2$-T15-Tag8 |
| Tag-9 | NH$_2$-T15-TCCCTGTCTCGTTGCGTGTCTCGT (SEQ ID NO: 9) | NH$_2$-T15-Tag9 |
| Tag-10 | NH$_2$-T15-GTTAGGGTCGCGCCAAACTCTCC (SEQ ID NO: 10) | NH$_2$-T15-Tag10 |
| Tag-11 | NH$_2$-T15-AGCTAGACCACTCAGCAGACTG (SEQ ID NO: 11) | NH$_2$-T15-Tag11 |
| Tag-12 | NH$_2$-T15-CGCCTTAGACAGCTTGCTCATG (SEQ ID NO: 12) | NH$_2$-T15-Tag12 |

The probes in Table 1 were dissolved in sample buffer, printed on the surface of aldehyde-coated glass slides, and arranged as shown in FIG. 1A. The probes shown in darker color are used to detect corresponding wild-type alleles, and the other probes are used to detect corresponding mutant alleles, and each probe is repeated 3 times (i.e., in three rows on the microarray).

Figure 1B:
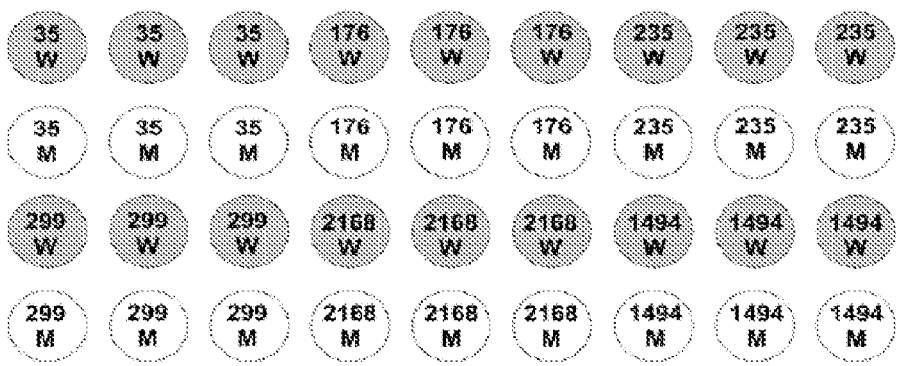

As shown in FIG. 1, the corresponding polymorphism sites detected by the probes in FIG. 1A are shown in FIG. 1B. In FIG. 1B, W indicates the probe is for the wild-type allele of the polymorphism site, and M indicates the probe is for the mutant allele of the polymorphism site.

The polymorphism sites are as follows:

The polymorphism sites c.35delG, c.176_191del16, c.235delC and c.299_300delAT are located on GJB2 (Cx26) gene (NM_004004.5, GI: 195539329).

The polymorphism site c.2168A>G is located on SLC26A4 (PDS) gene (NM_000441.1, GI: 4505696).

The polymorphism site m.1494C>T is located on 12S rRNA (MTRNR1, belonging to the mitochondrial genes) gene (NC_012920, GI: 251831106).

Wild-type or mutant polymorphism sites are as follows:

The mutation of "c.35delG" is located on the GJB2 gene. From the 5' end of the coding region, if the 35th nucleotide G is deleted, the allele is a c.35delG mutant. Otherwise the allele is wild-type.

The mutation of "c.176_191del16" is located on GJB2 gene. From the 5' end of the coding region, if the 16 consecutive nucleotides from the 176th nucleotide to 191th nucleotide are deleted, the allele is a c.176_191del16 mutant. Otherwise the allele is wild-type.

The mutation of "c.235delC" is located on GJB2 gene. From the 5' end of the coding region, if the 235th nucleotide C is deleted, the allele is a c.235delC mutant. Otherwise the allele is wild-type.

The mutation of "c.299_300delAT" is located on GJB2 gene. From the 5' end of the coding region, if the 2 consecutive nucleotides from the 299th nucleotide to 300th nucleotide are deleted, the allele is a c.299_300delAT mutant. Otherwise the allele is wild-type.

The mutation of "c.2168A>G" is located on SLC26A4 gene. From the 5' end of the coding region, if the 2168th nucleotide A is mutated to G, the allele is a c.2168A>G mutant. Otherwise the allele is wild-type.

The mutation of "m.1494C>T" is located on the 12S RNA gene. If the 1494th nucleotide C is mutated to T, the allele is a m.1494C>T mutant. Otherwise the allele is wild-type.

In FIG. 1B, 35W indicates the wild-type probe of c.35delG (Tag1), 176W indicates the wild-type probe of c.176_191del16 (Tag3), 235W indicates the wild-type probe of c.235delC (Tag5), 35M indicates the mutant probe of c.35delG (Tag2), 176M indicates the mutant probe of c.176_191del16 (Tag4), 235M indicates the mutant probe of c.235delC (Tag6), 299W indicates the wild-type probe of c.299_300delAT (Tag7), 2168W indicates the wild-type probe of c.2168A>G (Tag9), 1494W indicates the wild-type probe of m.1494C>T (Tag11), 299M indicates the mutant probe of c.299_300delAT (Tag8), 2168M indicates the mutant probe of c.2168A>G (Tag10), 1494M indicates the mutant probe of m.1494C>T (Tag12). Name with the 'W' or 'M' suffix represents the probe corresponding to the wild-type or mutant allele at the SNP/mutation locus, respectively. Tags 1-12 in FIG. 1A correspond to the above Tags 1-12, respectively.

Multiplex PCR primers used for analyzing a total of 6 SNPs/mutations are listed in Table 2. In column Mutation Type 'del' represents a deletion mutation, e.g., c.35delG means a deletion of G at position 35 in the coding region of GJB2; '>' represents a substitution mutation, e.g. c.2168A>G means a substitution of A by G at position 2168 in the coding region of SLC26A4 (PDS). Primer Name with 'WT' or 'MU' suffix represents an allele-specific primer capable of specifically amplifying the wild-type or mutant allele at the SNP/mutation locus, respectively. Primer Name with a 'RB' suffix represent a common primer, biotinylated at the 5'-termini, capable of amplifying both the wild-type allele and the mutant allele of the target genetic fragments including the SNP/mutation locus. For each SNP/mutation locus the two allele-specific primers respectively pair with the common primer.

TABLE 2

Hereditary deafness related SNP/ mutation and primers

| Mutation | Primer Name | Primer Sequence (5'→3') |
| --- | --- | --- |
| c.35delG | t35delG-WT | Tag1-TGTTTGTTCACACCCCCGAG (SEQ ID NO: 13) |
|  | t35delG-MU | Tag2-TGTTTGTTCACACCCGCAG (SEQ ID NO: 14) |
|  | 35dclG-RB | Biotin-GCATGCTTGCTTACCCAGAC (SEQ ID NO: 15) |
| c.176_191del16 | t176_191del16-WT | Tag3-CCAGGCTGCAAGAACGTGTG (SEQ ID NO: 16) |
|  | t176_191del16-MU | Tag4-ACCCTGCAGCCAGCTACG (SEQ ID NO: 17) |
|  | 176_191del16-RB | Biotin-GAGCCTTCGATGCGGACC (SEQ ID NO: 18) |
| c.235delC | t235delC-WT | Tag5-AAACGGCTATGGGCCCTG (SEQ ID NO: 19) |
|  | t235dclC-MU | Tag6-ATCCGGCTATGGGCCCTG (SEQ ID NO: 20) |
|  | 235delC-RB | Biotin-GAGCCTTCGATGCGGACC (SEQ ID NO: 21) |
| c.299_300delAT | t299-300delAT-WT | Tag7-TGGCCTACCGGAGACATGA (SEQ ID NO: 22) |
|  | t299-300delAT-MU | Tag8-CGTGGCCTACCGGAGACGA (SEQ ID NO: 23) |
|  | 299-300delAT-RB | Biotin-GAGCCTTCGATGCGGACC (SEQ ID NO: 24) |
| c.2168A > G | t2168A > G-WT | Tag9-GACACATTCTTTATGACGGTCCA (SEQ ID NO: 25) |
|  | t2168A > G-MU | Tag10-ACATTCTTTTTGTCGGTCCG (SEQ ID NO: 26) |
|  | 2168A > G-RB | Biotin-CAAGGTTTTCCAGATTGCTGAG (SEQ ID NO: 27) |
| m.1494C > T | t1494C > T-WT | Tag11-CTTTGAAAGTATACTTGAGGAGG (SEQ ID NO: 28) |
|  | t1494C > T-MU | Tag12-CTTTGAAGTATACTTGAGGAGA (SEQ ID NO: 29) |
|  | 1494C > T-RB | Biotin-CCCTGATGAAGGCTACAAAG (SEQ ID NO: 30) |

For each polymorphism locus, there are two allele-specific primers and a common biotin-labeled primer. The allele-specific primers comprise two parts, namely, a tag sequence at the 5' end, and a nucleotide sequence in the 5'-3' direction that is complementary to target gene locus. For each SNP/mutation locus the two allele-specific primers respectively pair with the common primer. Thus, the allele specific primers and common primer can be used in multiple allele-specific PCR amplifications to amplify the polymorphism locus DNA fragments.

In Table 2, there are 18 primers that are used for multiple allele-specific PCR amplifications.

In specific examples, the MyOne Dynal magnetic beads were coated by streptavidin (Invitrogen Dynal AS, Oslo, Norway), with particle size being 1 micron in diameter. The particle coated with streptavidin can be used to capture the biotin-labeled DNA fragments.

In specific examples, the hybridization buffer was prepared as follows. The buffer comprises a solvent and a solute, the solute being SDS, and the solvent being $H_2O$, SSC, Denhardt's and formamide. The hybridization buffer contains 0.15% SDS (0.15 g/100 ml), SSC (9x), Denhardt's (7.5x), and formamide (37.5% v/v). The hotstar polymerase and the buffer were from Promega Corporation, catalogue number M500x.

Example 1: Method of Detecting Luminophore-Labeled Target Molecules

In this example, whole genome DNA was used as the template for PCR reaction to amplify target molecules.

Step I: The genomic DNA was extracted from whole blood from individuals who have been genotyped as normal. The genomic DNA was subject to multiple allele-specific PCR amplifications using the 18 primers listed in Table 2, to achieve the enrichment of DNA fragments at multiple polymorphism sites.

Step II: Single-stranded DNA was prepared using the MyOne Dynal magnetic beads in accordance with the instruction manual. 3 μl MyOne Dynal magnetic beads were pipetted into 8 μl of the amplified product, and the mixture was incubated for 10 min. The magnetic beads were then treated with freshly prepared NaOH solution (0.1 M) for 10 min. The NaOH solution was then removed, and 15 μl of hybridization buffer was added to form the hybridization mixture to be applied to a microarray.

Step III: The hybridization mixture was then applied to the microarray chip, and incubated for 1 hour at 50° C. If the magnetic beads were manipulated by magnetic force, the hybridization incubation time can be reduced to 15 min. The microarray chip was then washed with buffer I and buffer II once each at room temperature. Wash buffer I was 1xPBS with 0.2% Tween-20 (v/v), and wash buffer II was 0.03x SSC. The chip was then dried by centrifugation, and scanned with a commercial fluorescent microarray scanner (or eye observation). The scanner was LuxScan 10K from Capitalbio Corporation, Beijing. The laser power was 90%, and photomultiplier (PMT) was 600. The images were analyzed using SpotData (Capitalbio Corporation, Beijing).

When normal human genome DNA was used as template in the PCR, all the primers specific for the mutation sites would not amplify, and no PCR products were generated that specifically hybridized to the mutant-specific microarray probes. Wild-type primers would amplify the wild-type target sequences, and the PCR products after multiple rounds of amplification in the PCR reactions contained 6 kinds of oligonucleotide fragments (corresponding to 6 wild-type sites for each of the following loci: c.35delG, c.176_191del16, c.235delC, c.299_300delAT, c.2168A>G and m.1494C>T). These oligonucleotide fragments were hybridized with the wild-type probes on the microarray chip. The oligonucleotide fragments coupled to the microparticles were labeled with a luminophore according to the examples below, and subjected to hybridization on the microarray to probes that corresponded to the 35W, 176W, 235W, 299W, and 1494W positions. Through hybridization, the oligonucleotide fragments labeled with the luminophore were immobilized on the microarray chip, and the fluorescent signals were detected by the scanner at the positions where specific target-probe hybrization took place.

Example 2: Labeling Target Molecules by Labeling a Subset of Target Molecules with a Luminophore In this example, a plurality of target molecules were labeled by labeling one type of target molecule in the plurality of target molecules. The PCR primers used in this example were identical to those in Table 2, except that the primer 35delG-RB was labeled with the luminophore Cy3 (identified by * in Table 3).

TABLE 3

| Mutation | Primer Name | Primer Sequence (5'→3') |
|---|---|---|
| c.35delG | t35delG-WT | Tag1-TGTTTGTTCACACCCCCGAG (SEQ ID NO: 13) |
| | t35delG-MU | Tag2-TGTTTGTTCACACCCGCAG (SEQ ID NO: 14) |
| | 35delG-RB | Biotin-GCAT*GCTTGCTTACCCAGAC (SEQ ID NO: 15) |

Primer 35delG-RB labeled with luminophore

The PCR primers were used to amplify and enrich the polymorphism site DNA fragments using normal human genome DNA as template. The PCR reaction system was set up according to Table 4, and the PCR amplification cycle is shown in Table 5.

TABLE 4

PCR system

| Reagent Name | Volume(μl) | Concentration |
|---|---|---|
| ddH$_2$O | 13.4 | / |
| 2.5 mM dNTP | 2 | 0.2 mM |
| 5 × buffer | 5 | 1 × buffer |
| 25 mM MgCl$_2$ | 1 | 1 mM |
| Hotstar polymerase (5 U/μl) | 0.2 | 0.04 U/μl |
| specific primers mix (the same concentration) | 1.2 | 1.2 μM |
| common primers mix (the same concentration) | 1.2 | 1.2 μM |
| Human DNA(10 ng/μl) | 1 | 0.4 ng/μl |
| total | 25 | / |

TABLE 5

PCR Amplification Cycle

| Temp. (° C.) | 95 | 95 | 55 | 72 | 72 | 12 |
|---|---|---|---|---|---|---|
| time (s) | 600 | 30 | 15 | 130 | 600 | forever |
| cycle | 1 | | 35 | | 1 | |

The MyOne Dynal magnetic beads used in this example were coated by streptavidin. Preparation of single-stranded DNA and hybridization to the microarray were performed according to Step II and Step III of Example 1 above. The results of microarray chip scanning are shown in FIG. 2.

Figure 2:
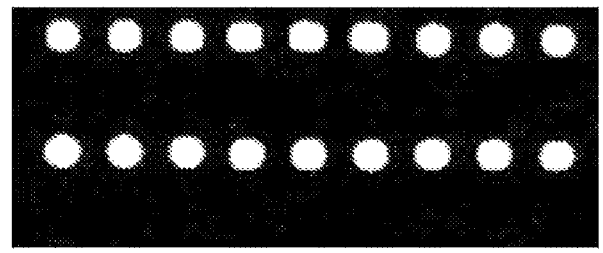
FIG. 2 shows the result of microarray chip scanning, according to a method depicted in FIG. 3. Hybridization signals are detected in the first and third lines corresponding to the wild-type probes.

The arrangement of probes in FIG. 2 corresponds to the location of probes in FIG. 1A or FIG. 1B. The hybridization signals were detected in the first and third lines. For example, in the arrangement of probes shown in FIG. 1B, only the probes in the first and third lines (the wild-type probes) emitted specific hybridization signals, as shown in FIG. 2.

Figure 3:
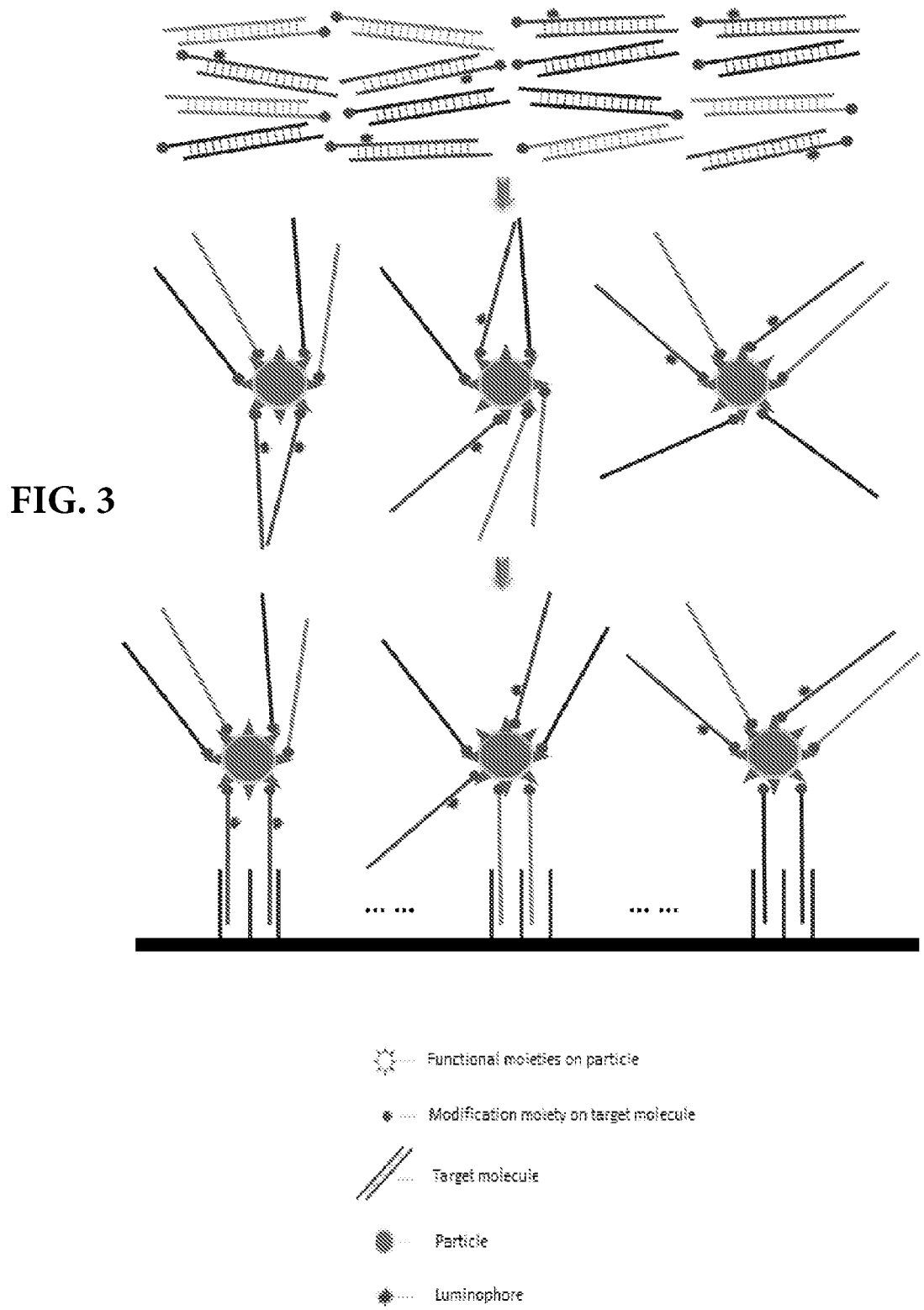
FIG. 3 is a schematic depicting a method comprising labeling a subset of a plurality of target molecules with a luminophore, thereby directly or indirectly labeling the plurality of target molecules with the luminophore, according to one aspect of the present disclosure.

In this example, the target molecules were labeled with the luminophore, wherein only a subset of the target molecules was directly labeled with the luminophore. The results in FIG. 2 indicate that such a labeling method (as illustrated in FIG. 3) can be used to label a plurality of target molecules for them to be detected and analyzed using a microarray chip.

Example 3: Labeling the Surface of a Particle with a Luminophore

In this example, the Streptavidin moieties on the surface of the particle were labeled with the luminophore Cy3.

The PCR primers listed in Table 2 were used to amplify and enrich the polymorphism site DNA fragments using normal human genome DNA as template, by allele-specific PCR. The PCR reaction system was set up according to Table 4, and the PCR amplification cycle is shown in Table 5.

Preparation of single-stranded DNA and hybridization to the microarray were performed according to Step II and Step III of Example 1 above. The results of microarray chip scanning are shown in FIG. 4.

Figure 4:
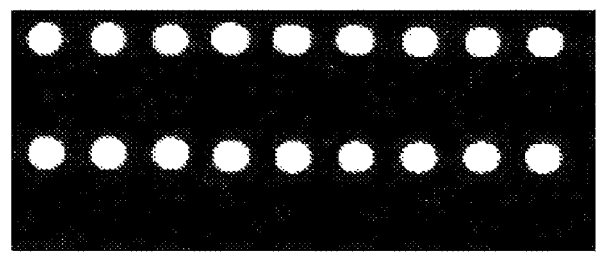
FIG. 4 shows the result of microarray chip scanning, according to a method depicted in FIG. 5. Hybridization signals are detected in the first and third lines corresponding to the wild-type probes.

The arrangement of probes in FIG. 4 corresponds to the location of probes in FIG. 1A or FIG. 1B. The hybridization signals were detected in the first and third lines. For example, in the arrangement of probes shown in FIG. 1B, only the probes in the first and third lines (the wild-type probes) emitted specific hybridization signals, as shown in FIG. 4.

Figure 5:
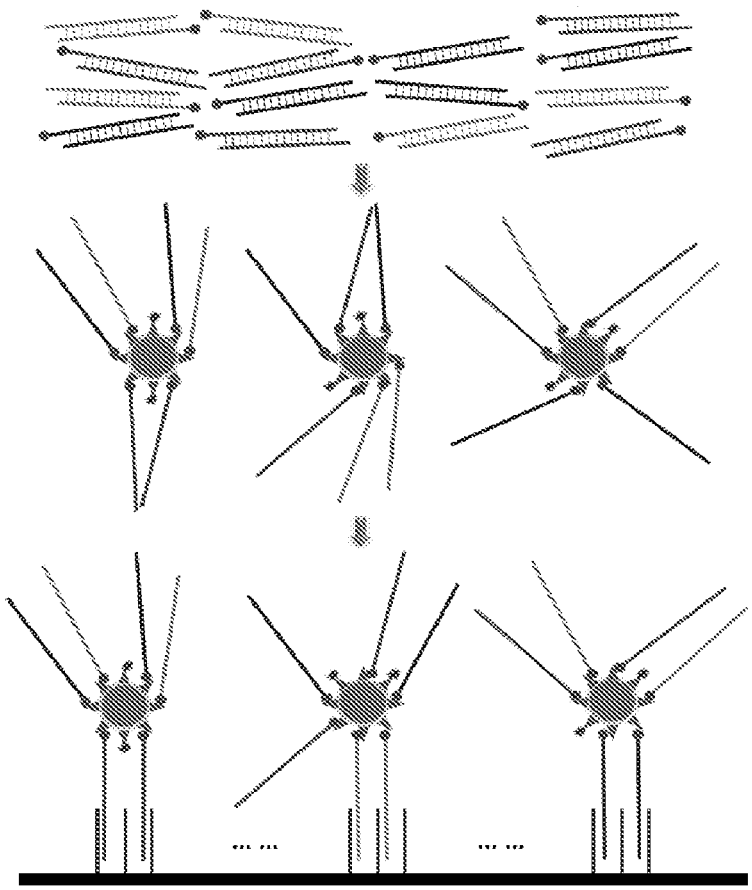
FIG. 5 is a schematic depicting a method comprising labeling a subset of the functional moieties of a particle with a luminophore, thereby indirectly labeling the plurality of target molecules with the luminophore, according to one aspect of the present disclosure.

In this example, the luminophore was used to label the Streptavidin on the surface of the microparticles. The results in FIG. 4 indicate that such a labeling method (as illustrated in FIG. 5) can be used to label a plurality of target molecules for them to be detected and analyzed using a microarray chip.

Example 4: Labeling a Microparticle by Introducing a Luminophore into or onto the Microparticle In this example, the luminophore Cy3 was introduced into or onto microparticles coated with Streptavidin. In one experiment, the luminophore Cy3 was mixed into the microparticles, wherein the microparticles were coated with Streptavidin.

The PCR primers listed in Table 2 were used to amplify and enrich the polymorphism site DNA fragments using normal human genome DNA as template, by allele-specific PCR. The PCR reaction system was set up according to Table 4, and the PCR amplification cycle is shown in Table 5.

Preparation of single-stranded DNA and hybridization to the microarray were performed according to Step II and Step III of Example 1 above. The results of microarray chip scanning are shown in FIG. 6.

Figure 6:
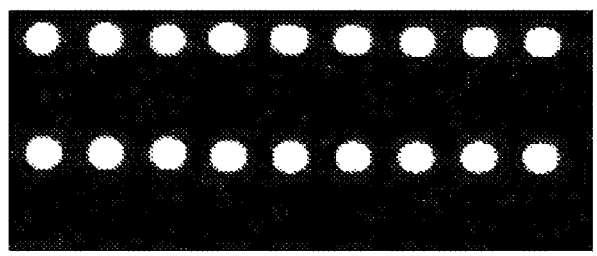
FIG. 6 shows the result of microarray chip scanning, according to a method depicted in FIG. 7. Hybridization signals are detected in the first and third lines corresponding to the wild-type probes.

The arrangement of probes in FIG. 6 corresponds to the location of probes in FIG. 1A or FIG. 1B. The hybridization signals were detected in the first and third lines. For example, in the arrangement of probes shown in FIG. 1B, only the probes in the first and third lines (the wild-type probes) emitted specific hybridization signals, as shown in FIG. 6.

Figure 7:
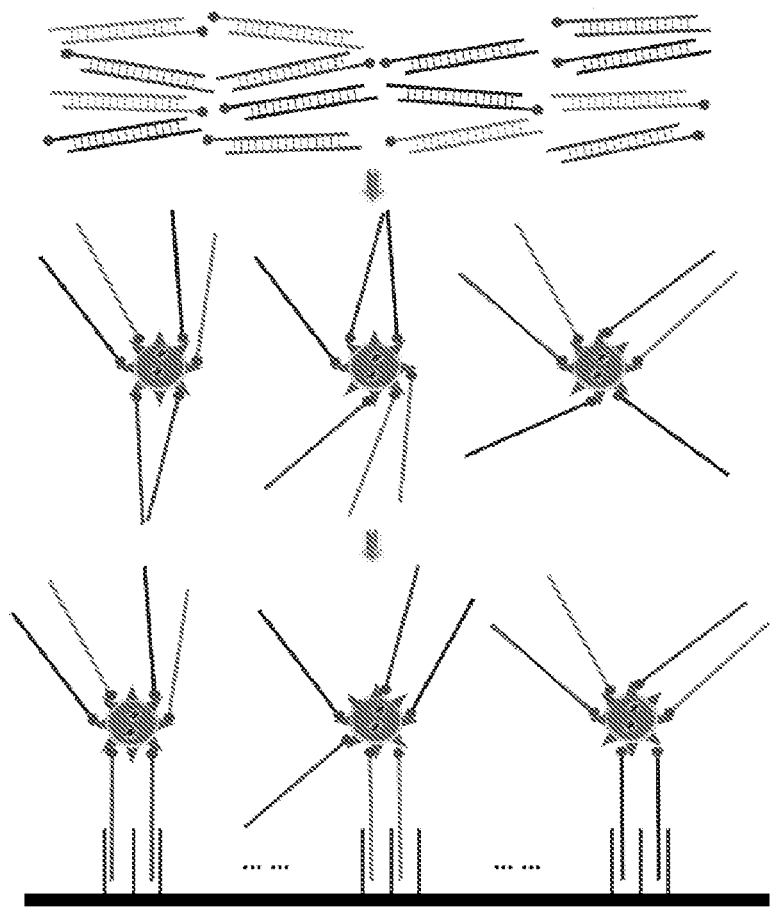
FIG. 7 is a schematic depicting a method comprising introducing a luminophore into or onto a particle to label the particle, thereby indirectly labeling the plurality of target molecules with the luminophore, according to one aspect of the present disclosure.

In this example, the luminophore was introduced into or onto the microparticles. The results in FIG. 6 indicate that such a labeling method (as illustrated in FIG. 7) can be used to label a plurality of target molecules for them to be detected and analyzed using a microarray chip.

Example 5: Using a Labeling Molecule to Label a Plurality of Target Molecules In this example, a labeling molecule SP1 was synthesized and used to label a plurality of target molecules. The sequence of SP1 is shown in Table 6.

TABLE 6

Sequence of labeling molecule SP1

| Name | Sequence (5'→3') |
|---|---|
| SP1 | Biotin-*GCACGCTATCACGTTAGAC (SEQ ID NO: 31) |

The luminophore Cy3 was used to label the dGTP in the sequence of SP1, identified by * in Table 6.

The PCR primers listed in Table 2 were used to amplify and enrich the polymorphism site DNA fragments using normal human genome DNA as template, by allele-specific PCR. The PCR reaction system was set up according to Table 4, and the PCR amplification cycle is shown in Table 5.

In this example, the magnetic beads were coated by Streptavidin.

Preparation of single-stranded DNA and hybridization to the microarray were performed according to Step II and Step III of Example 1 above, except that the procedures included incubating the PCR products with the treated microparticles (3 μL), SP1 (1 μL, final concentration 0.1 μM), and 8 μl of the amplified products for 10 minutes. The results of microarray chip scanning are shown in FIG. 8.

Figure 8:
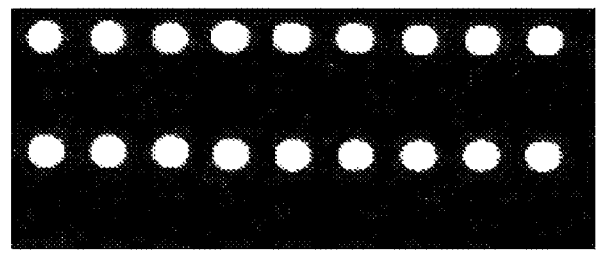
FIG. 8 shows the result of microarray chip scanning, according to a method depicted in FIG. 9. Hybridization signals are detected in the first and third lines corresponding to the wild-type probes.

The arrangement of probes in FIG. 8 corresponds to the location of probes in FIG. 1A or FIG. 1B. The hybridization signals were detected in the first and third lines. For example, in the arrangement of probes shown in FIG. 1B, only the probes in the first and third lines (the wild-type probes) emitted specific hybridization signals, as shown in FIG. 8.

Figure 9:
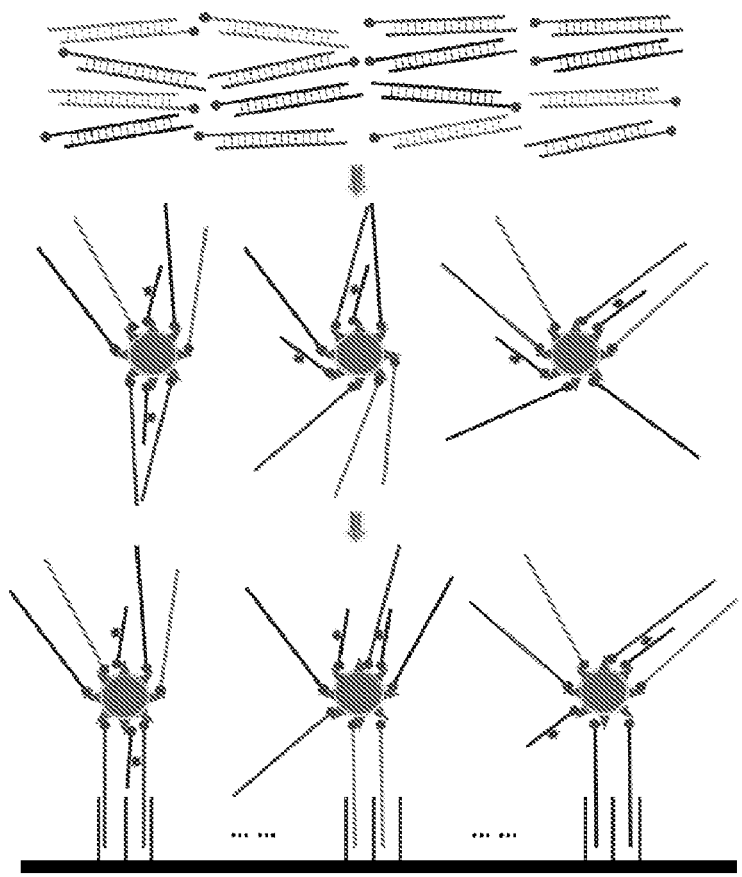
FIG. 9 is a schematic depicting a method comprising providing a labeling molecule comprising a luminophore and a modification moiety capable of interacting with the functional moiety of a particle, thereby indirectly labeling the plurality of target molecules with the luminophore, according to one aspect of the present disclosure.

In this example, the luminophore was present on a labeling molecule SP1, which, like the biotin-labeled target molecules, specifically binds to the streptavidin on the microparticles. The results in FIG. 8 indicate that such a labeling method (as illustrated in FIG. 9) can be used to label a plurality of target molecules for them to be detected and analyzed using a microarray chip.

Example 6: Using a Binding Molecule to Label a Plurality of Target Molecules In this example, a binding molecule C1494 was synthesized and used to label a plurality of target molecules. The sequence of C1494 is shown in Table 7, and the C1494 sequence is complement to sequences of products of the m.1494C>T loci by PCR.

TABLE 7

Sequence of binding molecule C1494

| Name | Sequence (5'→3') |
|---|---|
| C1494 | ACT*TACCATGTTACGACTAGT (SEQ ID NO: 32) |

The luminophore Cy3 was used to label the dTTP in the sequence of C1494, identified by * in Table 7.

In this example, the magnetic beads were coated by Streptavidin.

Preparation of single-stranded DNA and hybridization to the microarray were performed according to Step II and Step III of Example 1 above, except that the procedures included mixing the hybridization mixture with C1494 (final concentration 0.1 μM) before applying the mixture to the microarray for incubation at 50° C. for 1 hr. The results of microarray chip scanning are shown in FIG. 10.

Figure 10:
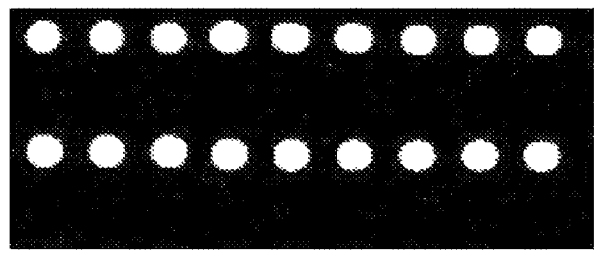
FIG. 10 shows the result of microarray chip scanning, according to a method depicted in FIG. 11. Hybridization signals are detected in the first and third lines corresponding to the wild-type probes.

The arrangement of probes in FIG. 10 corresponds to the location of probes in FIG. 1A or FIG. 1B. The hybridization signals were detected in the first and third lines. For example, in the arrangement of probes shown in FIG. 1B, only the probes in the first and third lines (the wild-type probes) emitted specific hybridization signals, as shown in FIG. 10.

Figure 11:
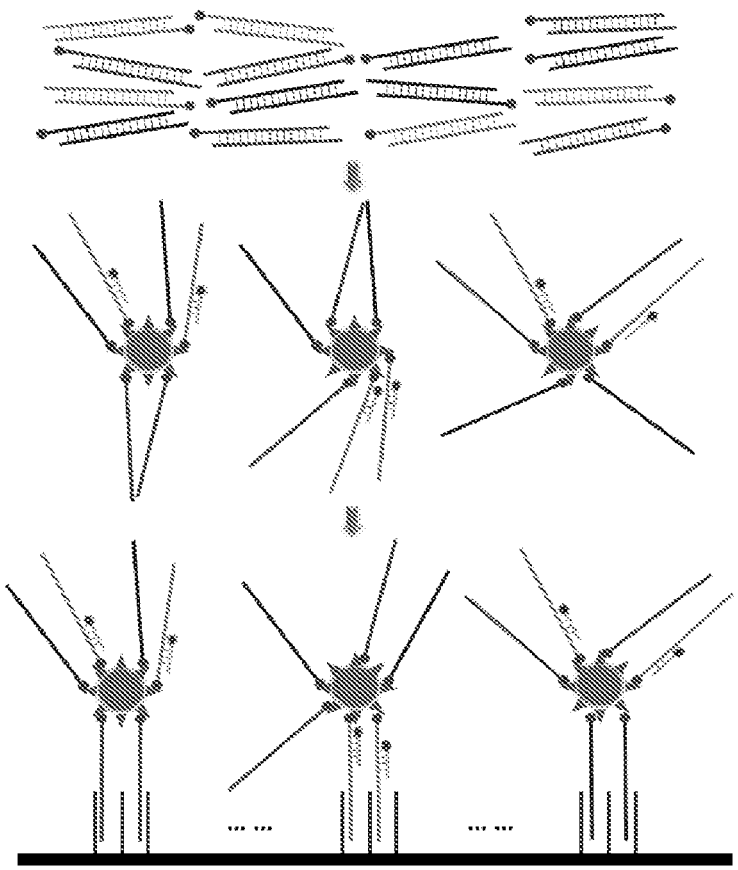
FIG. 11 is a schematic depicting a method comprising providing a binding molecule comprising a luminophore and capable of specific binding to a subset of a plurality of target molecules, thereby indirectly labeling the plurality of target molecules with the luminophore, according to one aspect of the present disclosure.

In this example, the luminophore was present on a binding molecule C1494, which specifically hybridizes to a subset of target molecules of a plurality of target molecules. The results in FIG. 10 indicate that such a labeling method (as illustrated in FIG. 11) can be used to label a plurality of target molecules for them to be detected and analyzed using a microarray chip.

The invention claimed is:

1. A composition comprising:

a plurality of target polynucleotides, a subset of which is labeled with a luminophore, wherein each of the target polynucleotides comprises a modification moiety and a portion capable of specific binding to an immobilized probe molecule on a microarray; and a particle comprising a plurality of functional moieties capable of interacting with the modification moieties of the target polynucleotides, wherein the plurality of target polynucleotides are coupled to the particle via interaction between the modification moieties and the functional moieties to form a target-particle complex that comprises target molecule(s) labeled with the luminophore and target molecule(s) not labeled with the luminophore, and wherein the plurality of target polynucleotides are directly or indirectly labeled with the luminophore.

2. A composition comprising:

a plurality of target polynucleotides, wherein each of the target polynucleotides comprises a modification moiety and a portion capable of specific binding to an immobilized probe molecule on a microarray;

a particle comprising a plurality of functional moieties capable of interacting with the modification moieties of the target polynucleotides; and a binding molecule comprising a luminophore, wherein the binding molecule is capable of specific binding to a subset of the plurality of target polynucleotides, and wherein the binding molecule does not bind to the immobilized probe molecule on the microarray or directly to the particle, wherein the plurality of target polynucleotides are coupled to the particle via interaction between the modification moieties and the functional moieties, and wherein the plurality of target polynucleotides are indirectly labeled with the luminophore.

* * * * *

SEQUENCE LISTING

```
<160> NUMBER OF SEQ ID NOS: 32

<210> SEQ ID NO 1
<211> LENGTH: 22
<212> TYPE: DNA
<213> ORGANISM: Artificial Sequence
<220> FEATURE:
<223> OTHER INFORMATION: Probe sequence

<400> SEQUENCE: 1
gaggagatcg tagctggtgc at                                              22

<210> SEQ ID NO 2
<211> LENGTH: 22
<212> TYPE: DNA
<213> ORGANISM: Artificial Sequence
<220> FEATURE:
<223> OTHER INFORMATION: Probe sequence

<400> SEQUENCE: 2
tcgctgccaa ccgagaattg ca                                              22

<210> SEQ ID NO 3
<211> LENGTH: 22
<212> TYPE: DNA
<213> ORGANISM: Artificial Sequence
<220> FEATURE:
<223> OTHER INFORMATION: Probe sequence

<400> SEQUENCE: 3
gagcaagcgc aaacgcagta ct                                              22

<210> SEQ ID NO 4
<211> LENGTH: 22
<212> TYPE: DNA
<213> ORGANISM: Artificial Sequence
<220> FEATURE:
<223> OTHER INFORMATION: Probe sequence

<400> SEQUENCE: 4
gcatagacgt ggctcaactg tc                                              22

<210> SEQ ID NO 5
<211> LENGTH: 24
<212> TYPE: DNA
<213> ORGANISM: Artificial Sequence
<220> FEATURE:
<223> OTHER INFORMATION: Probe sequence

<400> SEQUENCE: 5
caaggcacgt cccagacgca tcaa                                            24

<210> SEQ ID NO 6
<211> LENGTH: 23
<212> TYPE: DNA
<213> ORGANISM: Artificial Sequence
```

```
<220> FEATURE:
<223> OTHER INFORMATION: Probe sequence

<400> SEQUENCE: 6
tcggcacgcg cgagatcacc atc                                               23

<210> SEQ ID NO 7
<211> LENGTH: 24
<212> TYPE: DNA
<213> ORGANISM: Artificial Sequence
<220> FEATURE:
<223> OTHER INFORMATION: Probe sequence

<400> SEQUENCE: 7
ttttcccgtc cgtcatcgct caag                                              24

<210> SEQ ID NO 8
<211> LENGTH: 24
<212> TYPE: DNA
<213> ORGANISM: Artificial Sequence
<220> FEATURE:
<223> OTHER INFORMATION: Probe sequence

<400> SEQUENCE: 8
ggtatcgcga ccgcatccca atct                                              24

<210> SEQ ID NO 9
<211> LENGTH: 24
<212> TYPE: DNA
<213> ORGANISM: Artificial Sequence
<220> FEATURE:
<223> OTHER INFORMATION: Probe sequence

<400> SEQUENCE: 9
tccctgtctc gttgcgtgtc tcgt                                              24

<210> SEQ ID NO 10
<211> LENGTH: 23
<212> TYPE: DNA
<213> ORGANISM: Artificial Sequence
<220> FEATURE:
<223> OTHER INFORMATION: Probe sequence

<400> SEQUENCE: 10
gttagggtcg cgccaaactc tcc                                               23

<210> SEQ ID NO 11
<211> LENGTH: 22
<212> TYPE: DNA
<213> ORGANISM: Artificial Sequence
<220> FEATURE:
<223> OTHER INFORMATION: Probe sequence

<400> SEQUENCE: 11
agctagacca ctcagcagac tg                                                22

<210> SEQ ID NO 12
<211> LENGTH: 22
<212> TYPE: DNA
<213> ORGANISM: Artificial Sequence
<220> FEATURE:
<223> OTHER INFORMATION: Probe sequence

<400> SEQUENCE: 12
cgccttagac agcttgctca tg                                                22
```

```
<210> SEQ ID NO 13
<211> LENGTH: 20
<212> TYPE: DNA
<213> ORGANISM: Artificial Sequence
<220> FEATURE:
<223> OTHER INFORMATION: Primer sequence

<400> SEQUENCE: 13
tgtttgttca cacccccgag                                                 20

<210> SEQ ID NO 14
<211> LENGTH: 19
<212> TYPE: DNA
<213> ORGANISM: Artificial Sequence
<220> FEATURE:
<223> OTHER INFORMATION: Primer sequence

<400> SEQUENCE: 14
tgtttgttca cacccgcag                                                  19

<210> SEQ ID NO 15
<211> LENGTH: 20
<212> TYPE: DNA
<213> ORGANISM: Artificial Sequence
<220> FEATURE:
<223> OTHER INFORMATION: Primer sequence

<400> SEQUENCE: 15
gcatgcttgc ttacccagac                                                 20

<210> SEQ ID NO 16
<211> LENGTH: 20
<212> TYPE: DNA
<213> ORGANISM: Artificial Sequence
<220> FEATURE:
<223> OTHER INFORMATION: Primer sequence

<400> SEQUENCE: 16
ccaggctgca agaacgtgtg                                                 20

<210> SEQ ID NO 17
<211> LENGTH: 18
<212> TYPE: DNA
<213> ORGANISM: Artificial Sequence
<220> FEATURE:
<223> OTHER INFORMATION: Primer sequence

<400> SEQUENCE: 17
accctgcagc cagctacg                                                   18

<210> SEQ ID NO 18
<211> LENGTH: 18
<212> TYPE: DNA
<213> ORGANISM: Artificial Sequence
<220> FEATURE:
<223> OTHER INFORMATION: Primer sequence

<400> SEQUENCE: 18
gagccttcga tgcggacc                                                   18

<210> SEQ ID NO 19
<211> LENGTH: 18
<212> TYPE: DNA
<213> ORGANISM: Artificial Sequence
<220> FEATURE:
<223> OTHER INFORMATION: Primer sequence
```

```
<400> SEQUENCE: 19
aaacggctat gggccctg                                                   18

<210> SEQ ID NO 20
<211> LENGTH: 17
<212> TYPE: DNA
<213> ORGANISM: Artificial Sequence
<220> FEATURE:
<223> OTHER INFORMATION: Primer sequence

<400> SEQUENCE: 20
atccggctat gggcctg                                                    17

<210> SEQ ID NO 21
<211> LENGTH: 18
<212> TYPE: DNA
<213> ORGANISM: Artificial Sequence
<220> FEATURE:
<223> OTHER INFORMATION: Primer sequence

<400> SEQUENCE: 21
gagccttcga tgcggacc                                                   18

<210> SEQ ID NO 22
<211> LENGTH: 19
<212> TYPE: DNA
<213> ORGANISM: Artificial Sequence
<220> FEATURE:
<223> OTHER INFORMATION: Primer sequence

<400> SEQUENCE: 22
tggcctaccg gagacatga                                                  19

<210> SEQ ID NO 23
<211> LENGTH: 19
<212> TYPE: DNA
<213> ORGANISM: Artificial Sequence
<220> FEATURE:
<223> OTHER INFORMATION: Primer sequence

<400> SEQUENCE: 23
cgtggcctac cggagacga                                                  19

<210> SEQ ID NO 24
<211> LENGTH: 18
<212> TYPE: DNA
<213> ORGANISM: Artificial Sequence
<220> FEATURE:
<223> OTHER INFORMATION: Primer sequence

<400> SEQUENCE: 24
gagccttcga tgcggacc                                                   18

<210> SEQ ID NO 25
<211> LENGTH: 23
<212> TYPE: DNA
<213> ORGANISM: Artificial Sequence
<220> FEATURE:
<223> OTHER INFORMATION: Primer sequence

<400> SEQUENCE: 25
gacacattct ttatgacggt cca                                             23

<210> SEQ ID NO 26
```

```
<211> LENGTH: 20
<212> TYPE: DNA
<213> ORGANISM: Artificial Sequence
<220> FEATURE:
<223> OTHER INFORMATION: Primer sequence

<400> SEQUENCE: 26
acattctttt tgtcggtccg                                                    20

<210> SEQ ID NO 27
<211> LENGTH: 22
<212> TYPE: DNA
<213> ORGANISM: Artificial Sequence
<220> FEATURE:
<223> OTHER INFORMATION: Primer sequence

<400> SEQUENCE: 27
caaggttttc cagattgctg ag                                                 22

<210> SEQ ID NO 28
<211> LENGTH: 23
<212> TYPE: DNA
<213> ORGANISM: Artificial Sequence
<220> FEATURE:
<223> OTHER INFORMATION: Primer sequence

<400> SEQUENCE: 28
ctttgaaagt atacttgagg agg                                                23

<210> SEQ ID NO 29
<211> LENGTH: 22
<212> TYPE: DNA
<213> ORGANISM: Artificial Sequence
<220> FEATURE:
<223> OTHER INFORMATION: Primer sequence

<400> SEQUENCE: 29
ctttgaagta tacttgagga ga                                                 22

<210> SEQ ID NO 30
<211> LENGTH: 20
<212> TYPE: DNA
<213> ORGANISM: Artificial Sequence
<220> FEATURE:
<223> OTHER INFORMATION: Primer sequence

<400> SEQUENCE: 30
ccctgatgaa ggctacaaag                                                    20

<210> SEQ ID NO 31
<211> LENGTH: 19
<212> TYPE: DNA
<213> ORGANISM: Artificial Sequence
<220> FEATURE:
<223> OTHER INFORMATION: Labeling molecule sequence

<400> SEQUENCE: 31
gcacgctatc acgttagac                                                     19

<210> SEQ ID NO 32
<211> LENGTH: 18
<212> TYPE: DNA
<213> ORGANISM: Artificial Sequence
```

```
<220> FEATURE:
<223> OTHER INFORMATION: Binding molecule sequence

<400> SEQUENCE: 32
taccatgtta cgactagt                                              18
```